(12) United States Patent
Celentano et al.

(10) Patent No.: US 8,894,831 B2
(45) Date of Patent: Nov. 25, 2014

(54) PRINTED MEMORY ON STRIP

(75) Inventors: Michael J. Celentano, Fishers, IN (US); Herbert Harttig, Neustadt (DE); Brian A. Wittman, Indianapolis, IN (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 380 days.

(21) Appl. No.: 13/534,015

(22) Filed: Jun. 27, 2012

(65) Prior Publication Data
US 2014/0001043 A1    Jan. 2, 2014

(51) Int. Cl.
*G01N 27/327*    (2006.01)

(52) U.S. Cl.
USPC .................................. 204/403.02

(58) Field of Classification Search
CPC ..... G01N 27/327–27/3274; C12Q 1/00–1/006
USPC ........ 204/400, 403.01–403.015; 435/4–40.52
See application file for complete search history.

(56) References Cited

U.S. PATENT DOCUMENTS

| | | | |
|---|---|---|---|
| 3,584,183 A | 6/1971 | Chiaretta | |
| 3,671,948 A | 6/1972 | Cassen et al. | |
| 6,770,487 B2 | 8/2004 | Crosby | |
| 2005/0019945 A1 | 1/2005 | Groll et al. | |
| 2005/0019953 A1 | 1/2005 | Groll | |
| 2009/0125268 A1 | 5/2009 | Perry | |
| 2009/0134024 A1 | 5/2009 | Neel et al. | |
| 2010/0170791 A1 | 7/2010 | Lee | |
| 2011/0139635 A1 | 6/2011 | Huang et al. | |
| 2013/0027064 A1 | 1/2013 | Austera et al. | |

FOREIGN PATENT DOCUMENTS

| | | |
|---|---|---|
| EP | 1288653 | 3/2003 |
| EP | 2020596 | 2/2009 |
| EP | 2324767 | 5/2011 |

OTHER PUBLICATIONS

"Mass Printing of Polymer Diodes" Abstract Institute for Print and Media Technology, Chemnitz Univ. of Technology (undated).
"Effect of Dielectric Barrier On Rectification . . ." Journal of Physics D.; App. Phys. 44 (2011).
"Polymer-Based Rectifying Diodes on a Glass . . ."; Macromolecular Rapid Commun. (2005).

*Primary Examiner* — J. Christopher Ball
(74) *Attorney, Agent, or Firm* — Harness, Dickey & Pierce, P.L.C

(57) ABSTRACT

A test strip for analyzing a biological fluid using a test meter includes a biosensor to sense the biological fluid. The test strip includes contacts to communicate with the test meter and conductors connected to the contacts. The test strip further includes a combination of diodes, resistors, and short circuits arranged in various ways between the conductors. The test strip stores data based on a number of connections severed between the diodes, the resistors, the short circuits, and the conductors. The test meter reads the data and communicates with the biosensor via the contacts.

59 Claims, 17 Drawing Sheets

| Cut IDs | 1-A | A-1 | Notes |
|---|---|---|---|
| None | Short | Short | State 1 |
| 1 | Short | Short | |
| 3 | Short | Short | |
| 4 | Short | Short | |
| 6 | Short | Short | |
| 7 | Short | Short | |
| 9 | Short | Short | |
| 5 | Vdiode+ | Vdiode- | State 2 |
| 8 | Vdiode+ | Vdiode- | |
| 2 | Vdiode+ | Vdiode- | |
| All | Open | Open | State 3 |
| 2,5,8 | 3xVdiode+ | 3xVdiode- | State 4 |
| 2,5 | 2xVdiode+ | 2xVdiode- | State 5 |
| 5,8 | 2xVdiode+ | 2xVdiode- | |
| 2,8 | 2xVdiode+ | 2xVdiode- | |
| 1,2 | Open | Vdiode- | States 6 & 7 |
| 2,3 | Vdiode+ | Open | |
| 4,5 | Open | Vdiode- | |
| 5,6 | Vdiode+ | Open | |
| 7,8 | Open | Vdiode- | |
| 8,9 | Vdiode+ | Open | |
| or4or7,2,5,8, | 3xVdiode+ | Open | States 8 & 9 |
| or6or9,2,5,8, | Open | 3xVdiode- | |
| 1or4,2,5 | 2xVdiode+ | Open | States 10 & 11 |
| 3or6,2,5 | Open | 2xVdiode- | |
| multiple cuts | 3xVdiode+ | 2xVdiode- | States 12 & 13 |
| multiple cuts | 2xVdiode+ | 3xVdiode- | |
| multiple cuts | 3xVdiode+ | Vdiode- | States 14 & 15 |
| multiple cuts | Vdiode+ | 3xVdiode- | |
| multiple cuts | 2xVdiode+ | Vdiode- | States 16 & 17 |
| multiple cuts | Vdiode- | 2xVdiode+ | |

FIG. 2D

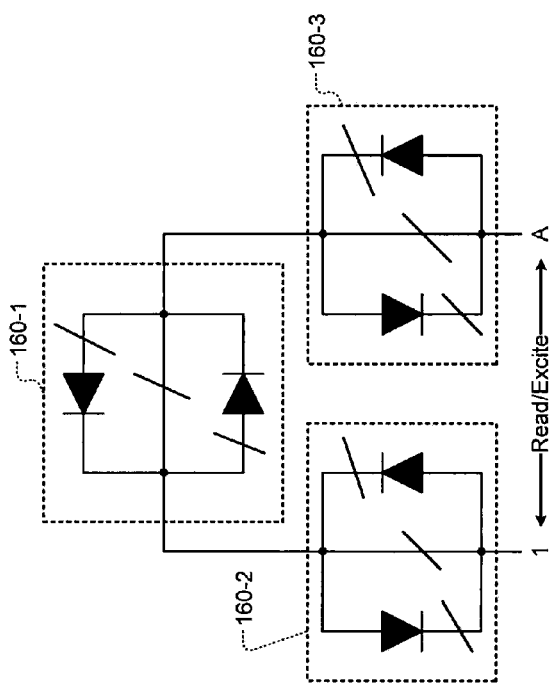

FIG. 2B

| Cut IDs | 1-A | 1-B | 2-A | 2-B | A-1 | A-2 | B-1 | B-2 | Notes |
|---|---|---|---|---|---|---|---|---|---|
| None | Short | Short | Short | Short | Short | Short | Short | Short | This section shows that any one of the 12 cuts will not change the state from defualt. |
| 1 | Short | Short | Short | Short | Short | Short | Short | Short | |
| 2 | Short | Short | Short | Short | Short | Short | Short | Short | |
| 3 | Short | Short | Short | Short | Short | Short | Short | Short | |
| 4 | Short | Short | Short | Short | Short | Short | Short | Short | |
| 5 | Short | Short | Short | Short | Short | Short | Short | Short | |
| 6 | Short | Short | Short | Short | Short | Short | Short | Short | |
| 7 | Short | Short | Short | Short | Short | Short | Short | Short | |
| 8 | Short | Short | Short | Short | Short | Short | Short | Short | |
| 9 | Short | Short | Short | Short | Short | Short | Short | Short | |
| 10 | Short | Short | Short | Short | Short | Short | Short | Short | |
| 11 | Short | Short | Short | Short | Short | Short | Short | Short | |
| 12 | Short | Short | Short | Short | Short | Short | Short | Short | |
| X=2,5,8,11 | Vdiode+ | Vdiode+ | Vdiode+ | Vdiode+ | Vdiode- | Vdiode- | Vdiode- | Vdiode- | This section shows that there are 2 virtual states (Vdiode or Open) for each of the virtual 8 digits. This will result in 2^8 states, 256, or an equivalent to 8 bits. |
| 1,X | Open | Vdiode+ | Vdiode+ | Vdiode+ | Vdiode- | Vdiode- | Vdiode- | Vdiode- | |
| 4,X | Vdiode+ | Open | Vdiode+ | Vdiode+ | Vdiode- | Vdiode- | Vdiode- | Vdiode- | |
| 7,X | Vdiode+ | Vdiode+ | Open | Vdiode+ | Vdiode- | Vdiode- | Vdiode- | Vdiode- | |
| 10,X | Vdiode+ | Vdiode+ | Vdiode+ | Open | Vdiode- | Vdiode- | Vdiode- | Vdiode- | |
| 3,X | Vdiode+ | Vdiode+ | Vdiode+ | Vdiode+ | Open | Vdiode- | Vdiode- | Vdiode- | |
| 6,X | Vdiode+ | Vdiode+ | Vdiode+ | Vdiode+ | Vdiode- | Open | Vdiode- | Vdiode- | |
| 9,X | Vdiode+ | Vdiode+ | Vdiode+ | Vdiode+ | Vdiode- | Vdiode- | Open | Vdiode- | |
| 12,X | Vdiode+ | Vdiode+ | Vdiode+ | Vdiode+ | Vdiode- | Vdiode- | Vdiode- | Open | |
| All | Open | Open | Open | Open | Open | Open | Open | Open | |
| 5,8,11 | Short | Vdiode+ | Vdiode+ | Vdiode+ | Short | Vdiode- | Vdiode- | Vdiode- | This section shows that there are only 4 unique states that come from the shorts. This will result in the additional 4 states beyond the 256 noted above, for a total of 260 states. |
| 2,8,11 | Vdiode+ | Short | Vdiode+ | Vdiode+ | Vdiode- | Short | Vdiode- | Vdiode- | |
| 2,5,11 | Vdiode+ | Vdiode+ | Short | Vdiode+ | Vdiode- | Vdiode- | Short | Vdiode- | |
| 2,5,8 | Vdiode+ | Vdiode+ | Vdiode+ | Short | Vdiode- | Vdiode- | Vdiode- | Short | |
| 2,5 | Short | Short | Short | Short | Short | Short | Short | Short | |
| 8,11 | Short | Short | Short | Short | Short | Short | Short | Short | |
| 2,8 | Short | Short | Short | Short | Short | Short | Short | Short | |
| 5,11 | Short | Short | Short | Short | Short | Short | Short | Short | |

FIG. 2C

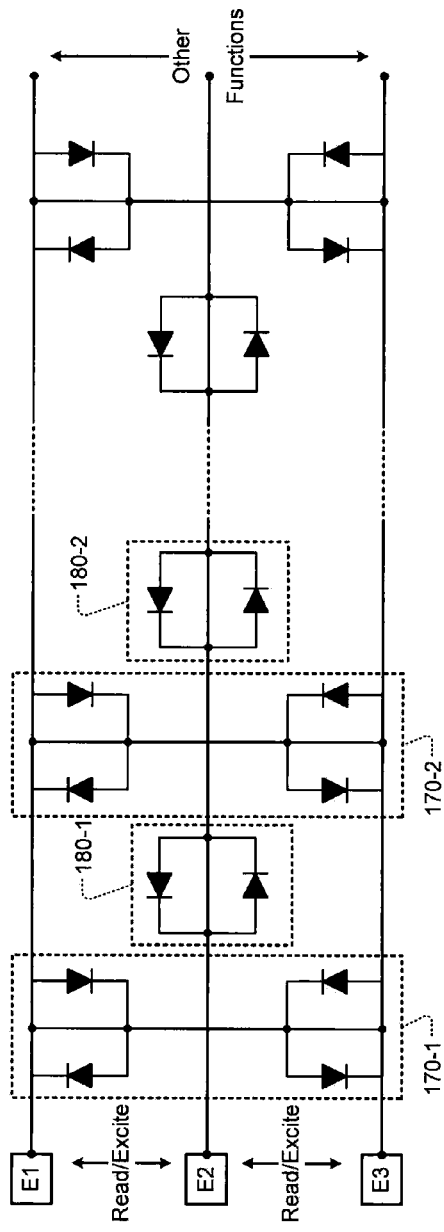
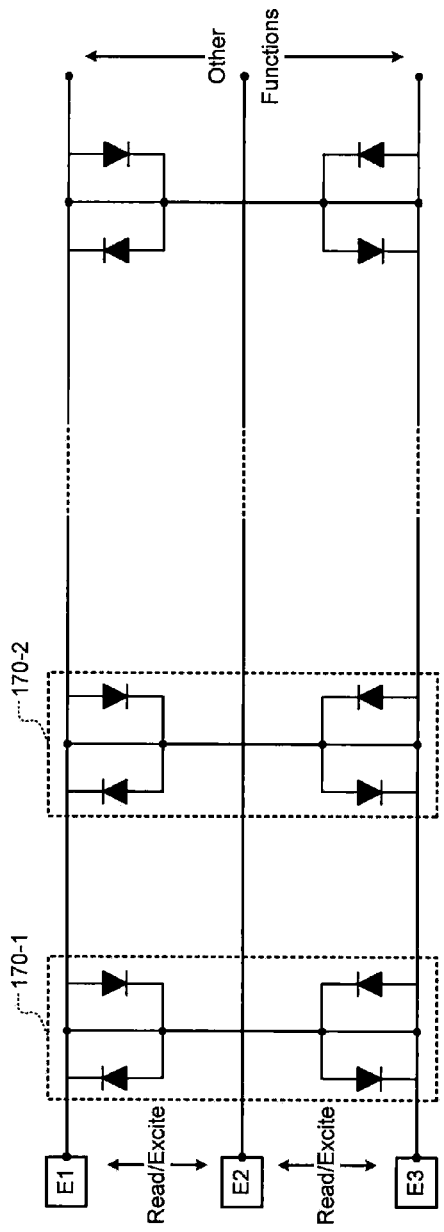
FIG. 3A
FIG. 3B

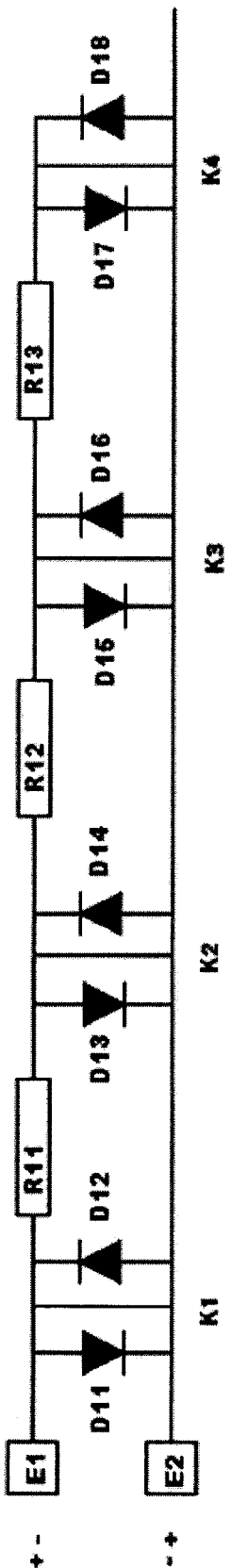

FIG. 4C

| status # | active elements | resistance at polarity 1 (+ -) | resistance at polarity 2 (- +) |
|---|---|---|---|
| 1 | D11 | D11F | D11R |
| 2 | D12 | D12R | D12F |
| 3 | D13 | R11+D13F | R11+D13R |
| 4 | D14 | R11+D14R | R11+D14F |
| 5 | D15 | R11+R12+D15F | R11+R12+D15R |
| 6 | D16 | R11+R12+D16R | R11+R12+D16F |
| 7 | D17 | R11+R12+R13+D17F | R11+R12+R13+D17R |
| 8 | D18 | R11+R12+R13+D18R | R11+R12+R13+D18F |
| 9 | D11+D12 | D11F*D12R/(D11F+D12R) | D11R*D12F/(D11R+D12F) |
| 10 | D11+D13 | D11F*(R11+D13F)/(D11F+(R11+D13F)) | D11R*(R11+D13R)/(D11R+(R11+D13R)) |
| 11 | D11+D14 | D11F*(R11+D14R)/(D11F+(R11+D14R)) | D11R*(R11+D14F)/(D11R+(R11+D14F)) |
| 12 | D11+D15 | D11F*(R11+R12+D15F)/(D11F+(R11+R12+D15F)) | D11R*(R11+R12+D15R)/(D11R+(R11+R12+D15R)) |
| 13 | D11+D16 | D11F*(R11+R12+D16R)/(D11F+(R11+R12+D16R)) | D11R*(R11+R12+D16F)/(D11R+(R11+R12+D16F)) |
| 14 | D11+D17 | D11F*(R11+R12+R13+D17F)/(D11F+(R11+R12+R13+D17F)) | D11R*(R11+R12+R13+D17R)/(D11R+(R11+R12+R13+D17R)) |
| 15 | D11+D18 | D11F*(R11+R12+R13+D18R)/(D11F+(R11+R12+R13+D18R)) | D11R*(R11+R12+R13+D18F)/(D11R+(R11+R12+R13+D18F)) |
| 16 | D12+D13 | D12R*(R11+D13F)/(D12R+(R11+D13F)) | D12F*(R11+D13R)/(D12F+(R11+D13R)) |
| 17 | D12+D14 | D12R*(R11+D14R)/(D12R+(R11+D14R)) | D12F*(R11+D14F)/(D12F+(R11+D14F)) |
| 18 | D12+D15 | D12R*(R11+R12+D15F)/(D12R+(R11+R12+D15F)) | D12F*(R11+R12+D15R)/(D12F+(R11+R12+D15R)) |
| 19 | D12+D16 | D12R*(R11+R12+D16R)/(D12R+(R11+R12+D16R)) | D12F*(R11+R12+D16F)/(D12F+(R11+R12+D16F)) |
| 20 | D12+D17 | D12R*(R11+R12+R13+D17F)/(D12R+(R11+R12+R13+D17F)) | D12F*(R11+R12+R13+D17R)/(D12F+(R11+R12+R13+D17R)) |
| 21 | D12+D18 | D12R*(R11+R12+R13+D18R)/(D12R+(R11+R12+R13+D18R)) | D12F*(R11+R12+R13+D18F)/(D12F+(R11+R12+R13+D18F)) |
| 22 | D13+D14 | R11+D13F*D14R/(D13F+D14R) | R11+D13R*D14F/(D13R+D14F) |
| 23 | D13+D15 | R11+D13F*(R12+D15F)/(D13F+(R12+D15F)) | R11+D13R*(R12+D15R)/(D13R+(R12+D15R)) |
| 24 | D13+D16 | R11+D13F*(R12+D16R)/(D13F+(R12+D16R)) | R11+D13R*(R12+D16F)/(D13R+(R12+D16F)) |
| 25 | D13+D17 | R11+D13F*(R12+R13+D17F)/(D13F+(R12+R13+D17F)) | R11+D13R*(R12+R13+D17R)/(D13R+(R12+R13+D17R)) |
| 26 | D13+D18 | R11+D13F*(R12+R13+D18R)/(D13F+(R12+R13+D18R)) | R11+D13R*(R12+R13+D18F)/(D13R+(R12+R13+D18F)) |
| 27 | D14+D15 | R11+(D14R*(R12+D15F)/(D14R+R12+D15F)) | R11+(D14F*(R12+D15R)/(D14F+R12+D15R)) |
| 28 | D14+D16 | R11+(D14R*(R12+D16R)/(D14R+R12+D16R)) | R11+(D14F*(R12+D16F)/(D14F+R12+D16F)) |
| 29 | D14+D17 | R11+(D14R*(R12+R13+D17F)/(D14R+R12+R13+D17F)) | R11+(D14F*(R12+R13+D17R)/(D14F+R12+R13+D17R)) |
| 30 | D14+D18 | R11+(D14R*(R12+R13+D18R)/(D14R+R12+R13+D18R)) | R11+(D14F*(R12+R13+D18F)/(D14F+R12+R13+D18F)) |
| 31 | D15+D16 | R11+R12+D15F*D16R/(D15F+D16R) | R11+R12+D15R*D16F/(D15R+D16F) |
| 32 | D15+D17 | R11+R12+D15F*(R13+D17F)/(D15F+(R13+D17F)) | R11+R12+D15R*(R13+D17R)/(D15R+(R13+D17R)) |
| 33 | D15+D18 | R11+R12+D15F*(R13+D18R)/(D15F+(R13+D18R)) | R11+R12+D15R*(R13+D18F)/(D15R+(R13+D18F)) |
| 34 | D16+D17 | R11+R12+D16R*(R13+D17F)/(D16R+(R13+D17F)) | R11+R12+D16F*(R13+D17R)/(D16F+(R13+D17R)) |
| 35 | D16+D18 | R11+R12+D16R*(R13+D18R)/(D16R+(R13+D18R)) | R11+R12+D16F*(R13+D18F)/(D16F+(R13+D18F)) |
| 36 | D17+D18 | R11+R12+R13+D17F*D18R/(D17F+D18R) | R11+R12+R13+D17R*D18F/(D17R+18F) |

| status # | active elements | resistance at polarity 1 ( + - ) | resistance at polarity 2 ( - + ) |
|---|---|---|---|
| 1 | K1 | 0 | 0 |
| 2 | K2 | R11 | R11 |
| 3 | K3 | R11+R12 | R11+R12 |
| 4 | K4 | R11+R12+R13 | R11+R12+R13 |
| 5 | K2+D11 | D11F*R11/(D11F+R11) | D11R*R11/(D11R+R11) |
| 6 | K2+D12 | D12R*R11/(D12R+R11) | D12F*R11/(D12F+R11) |
| 7 | K3+D11 | D11F*(R11+R12)/(D11F+R11+R12) | D11R*(R11+R12)/(D11R+R11+R12) |
| 8 | K3+D12 | D12R*(R11+R12)/(D12R+R11+R12) | D12F*(R11+R12)/(D12F+R11+R12) |
| 9 | K3+D13 | R11+D13F*R12/(D13F+R12) | R11+D13R*R12/(D13R+R12) |
| 10 | K3+K14 | R11+D14R*R12/(D14R+R12) | R11+D14F*R12/(D14F+R12) |
| 11 | K4+D11 | D11F*(R11+R12+R13)/(D11F*R11+R12+R13) | D11R*(R11+R12+R13)/(D11R*R11+R12+R13) |
| 12 | K4+D12 | D12R*(R11+R12+R13)/(D12R*R11+R12+R13) | D12F*(R11+R12+R13)/(D12F*R11+R12+R13) |
| 13 | K4+D13 | R11+D13F*(R12+R13)/(D13F+R12+R13) | R11+D13R*(R12+R13)/(D13R+R12+R13) |
| 14 | K4+D14 | R11+D13R*(R12+R13)/(D13R+R12+R13) | R11+D13R*(R12+R13)/(D13R+R12+R13) |
| 15 | K4+D15 | R11+D13R*(R12+R13)/(D13R+R12+R13) | R11+R12+D15R*R13/(D15R+R13) |
| 16 | K4+D16 | R11+R12+D16R*R13/(D16R+R13) | R11+R12+D16F*R13/(D16F+R13) |

FIG. 4D

| No. | Active | Resistance |
|---|---|---|
| 1 | D11 | RDD |
| 2 | D13 | RDD+R1 |
| 3 | D15 | RDD+R1+R2 |
| 4 | D17 | RDD+R1+R2+R3 |
| 5 | None | 1/3 RDS |
| 6 | D13+D15 | ((RDD+R1)*(RDD+R2))/(RDD+RDD+R1+R2) |
| 7 | D13+D17 | ((RDD+R1)*(RDD+R2+R3))/(RDD+RDD+R1+R2+R3) |
| 8 | D15+D17 | ((RDD+R1+R2)*(RDD+R3))/(RDD+RDD+R1+R2+R3) |
| 9 | D13+D15+D17 | (((((RDD+R1)*(RDD+R2))/((RDD+R1)*(RDD+R2))*(RDD+R3))/((((RDD+R1)*(RDD+R2))/(RDD+RDD+R1+R2))+RDD+R3) |

FIG. 5C

| Line Number | States | Bits | Useful States | Useful Bits |
|---|---|---|---|---|
| 1 | 53 | >5 | 32 | 5 |
| 2 | 2809 | >11 | 1024 | 10 |
| 3 | 148877 | >14 | 32768 | 15 |
| 4 | 7890481 | >22 | 1048576 | 20 |

FIG. 5D

PRINTED MEMORY ON STRIP

FIELD

The present disclosure relates generally to test strips used to analyze biological fluids and more particularly to incorporating memory to store data on the test strips.

BACKGROUND

Many test meters such as glucose meters use test strips to collect and analyze samples of biological fluids such as blood. To accurately analyze the samples, the test meters utilize a variety of information related to each strip. For example, the information includes reagent calibration data, expiration date of the test strip, models of test meters with which the test strip is compatible, and so on.

Presently, such information is placed in a memory device separate from the test strip, or a limited amount of information is placed on the test strips since cost of placing the information on the test strips can be prohibitive. The present disclosure relates to placing memory capable of storing large amounts of information on each test strip while minimizing cost and maximizing the amount of information that can be stored on each test strip.

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

SUMMARY

In a first embodiment, a test strip for analyzing a biological fluid using a test meter includes a biosensor to sense the biological fluid. First, second, and third contacts communicate with the test meter. First, second, and third conductors are connected to the first, second, and third contacts, respectively. First and second diodes each has a first end connected to the first conductor and a second end connected to the second conductor at a first node so that the first diode is connected to the second diode in opposing polarity. Third and fourth diodes each has a first end connected to the second conductor at the first node and a second end connected to the third conductor so that the third diode is connected to the fourth diode in opposing polarity. A first short circuit has (i) a first end connected to the first ends of the first and second diodes and (ii) a second end connected to the second ends of the first and second diodes. A second short circuit has (i) a first end connected to the first ends of the third and fourth diodes and (ii) a second end connected to the second ends of the third and fourth diodes. The test strip stores data based on a first number of connections severed between (i) the first through fourth diodes and the first through third conductors and (ii) the first and second ends of the first and second short circuits.

In a second embodiment, a test strip for analyzing a biological fluid using a test meter includes a biosensor to sense the biological fluid. First, second, and third contacts communicate with the test meter. First, second, and third conductors are connected to the first, second, and third contacts, respectively. First and second diodes each has a first end connected to the first conductor and a second end connected to the second conductor at a first node so that the first diode is connected to the second diode in opposing polarity. Third and fourth diodes each has a first end connected to the second conductor at the first node and a second end connected to the third conductor so that the third diode is connected to the fourth diode in opposing polarity. A resistance has a first end connected to the first node, and a second end. Fifth and sixth diodes each has a first end connected to the first conductor and a second end connected to the second end of the resistance at a second node so that the fifth diode is connected to the sixth diode in opposing polarity. Seventh and eighth diodes each has a first end connected to the second node and a second end connected to the third conductor so that the seventh diode is connected to the eighth diode in opposing polarity. The test strip is configured to store data based on a first number of connections severed between the first through eighth diodes and the first through third conductors.

In a third embodiment, a test strip for analyzing a biological fluid using a test meter includes a biosensor to sense the biological fluid. First and second contacts are configured to communicate with the test meter. First and second conductors are connected to the first and second contacts, respectively. A first resistance has a first end connected to the first contact, and a second end. First and second diodes each has a first end connected to the second end of the first resistance and a second end connected to the second conductor at a first node so that the first diode is connected to the second diode in opposing polarity. A second resistance has a first end connected to the second end of the first resistance, and a second end. Third and fourth diodes each has a first end connected to the second end of the second resistance and a second end connected to the second conductor at a second node so that the third diode is connected to the fourth diode in opposing polarity. The test strip is configured to store data based on a first number of connections severed between the first through fourth diodes and the first and second conductors.

In a fourth embodiment, a test strip for analyzing a biological fluid using a test meter includes a biosensor to sense the biological fluid. First and second contacts are configured to communicate with the test meter. First and second conductors are connected to the first and second contacts, respectively. A first plurality of diodes each has a first end connected to the first contact and a second end connected to the second contact. Junction areas of the first plurality of diodes are scaled according to a binary code. The test strip is configured to store data based on a first number of connections severed between the first plurality of diodes and the first and second conductors.

In a fifth embodiment, a test strip for analyzing a biological fluid using a test meter includes a biosensor to sense the biological fluid. First and second contacts are configured to communicate with the test meter. First and second conductors are connected to the first and second contacts, respectively. A first plurality of diodes each has a first end connected to the first contact and a second end. Junction areas of the first plurality of diodes are scaled according to a binary code. A first plurality of resistances each has a first end connected to the second end of a respective one of the first plurality of diodes and a second end connected to the second contact. The test strip is configured to store data based on a first number of connections severed between the first plurality of resistances and the first and second conductors.

In a sixth embodiment, a system for analyzing biological fluids includes a test strip and a mobile meter, where the test strip includes a biosensor to sense a biological fluid and a plurality of diodes that are connected to a plurality of contacts on the test strip and that are arranged in a network representing one of a plurality of states based on whether the diodes are short circuited, open circuited, or neither short circuited nor open circuited. The mobile meter is configured to supply excitation to a plurality of contacts on the test strip and measure response through the plurality of contacts, differentiate a plurality of voltage or current levels representing the plurality of states, and identify the one of the plurality of states represented by the network of diodes based on the measured current or voltage. The diodes are arranged in pairs, and in each of the pairs, (i) diodes are connected in parallel, (ii) an anode of a first diode is connected to a cathode of a second diode, and (iii) a cathode of the first diode is connected to an anode of the second diode. The mobile meter is configured to reverse polarity of the excitation supplied across the plurality of contacts on the test strip and measure response through the plurality of contacts. Junction areas of the diodes are scaled to a binary code. The system further includes a reference diode to calibrate the system in order to supply the excitation that is compensated for temperature and diode variations. The system further includes a plurality of resistors to enhance differentiation of the plurality of voltage or current levels representing the plurality of states. The resistors are binary-weighted. The mobile meter is configured to communicate with the biosensor via at least one of the plurality contacts used to communicate with the diodes. A portion of the plurality of states stores calibration information to be used by the mobile meter.

In a seventh embodiment, a system includes a test strip and a mobile meter, where the test strip includes a biosensor to sense a biological fluid and a plurality of diodes that are connected to a plurality of contacts on the test strip and that are arranged in a network representing one of a plurality of states based on whether the diodes are open circuited or not, and where junction areas of the diodes are scaled to a binary code. The mobile meter is configured to supply excitation to a plurality of contacts on the test strip and measure response through the plurality of contacts, where the response is distinct for each diode or a combination of diodes open circuited. The diodes are arranged in pairs, and in each of the pairs, (i) diodes are connected in parallel, (ii) an anode of a first diode is connected to a cathode of a second diode, and (iii) a cathode of the first diode is connected to an anode of the second diode. The mobile meter is configured to reverse polarity of the excitation supplied across the plurality of contacts on the test strip and measure response through the plurality of contacts. The system further includes a reference diode to calibrate the system in order to supply the excitation that is compensated for temperature and diode variations. The system further includes a plurality of resistors to enhance differentiation of current for each diode or a combination of diodes open circuited. The resistors are binary-weighted. The mobile meter is configured to communicate with the biosensor via at least one of the plurality contacts used to communicate with the diodes. A portion of the plurality of states stores calibration information to be used by the mobile meter.

In an eighth embodiment, a system includes a test strip and a mobile meter, where the test strip includes a biosensor to sense a biological fluid and a plurality of diodes and a plurality of resistors that are connected to a plurality of contacts on the test strip and that are arranged in a network representing one of a plurality of states based on whether the diodes are short circuited, open circuited, or neither short circuited nor open circuited. The mobile meter is configured to supply excitation to a plurality of contacts on the test strip and measure response through the plurality of contacts, where the response is distinct for each diode or a combination of diodes open circuited. The diodes are arranged in pairs, and in each of the pairs, (i) diodes are connected in parallel, (ii) an anode of a first diode is connected to a cathode of a second diode, and (iii) a cathode of the first diode is connected to an anode of the second diode. In each of the pairs, a short circuit is selectively included across the first and second diodes, and the response is distinct for each diode or a combination of diodes short circuited. The mobile meter is configured to reverse polarity of the excitation supplied across the plurality of contacts on the test strip and measure response through the plurality of contacts. The resistors enhance differentiation of current for each diode or a combination of diodes open circuited. The resistors are binary-weighted. The system further includes a reference diode to calibrate the system in order to supply the excitation that is compensated for temperature and diode variations. The mobile meter is configured to communicate with the biosensor via at least one of the plurality contacts used to communicate with the diodes and resistors. A portion of the plurality of states stores calibration information to be used by the mobile meter.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF DRAWINGS

The present disclosure will become more fully understood from the detailed description and the accompanying drawings, wherein:

FIG. 2B is a schematic of a memory architecture including an arrangement of diodes and short circuits that can be used to represent data;

FIG. 2C depicts a logic table for the memory architecture shown in FIG. 2A;

FIG. 2D depicts a logic table for the memory architecture shown in FIG. 2B;

FIG. 3A is a schematic of a memory architecture including an arrangement of diodes and short circuits that can be used to represent data on a test strip;

FIG. 3B is a schematic of a memory architecture including an arrangement of diodes and short circuits that can be used to represent data on a test strip;

FIG. 4A is a schematic of a basic ladder structure that forms a building block for memory architectures;

FIGS. 4B-4D depict tables of possible states when one or more diodes short circuits in FIG. 4A are activated;

FIG. 5C depicts a table of possible output resistances of one line shown in FIG. 5A or 5B;

FIG. 5D depicts a table of number of lines and memory capacities;

DESCRIPTION

The present disclosure relates to printing an array of active and passive components such as diodes, resistors, and short circuits ("shorts") on test strips using reel-to-reel processes. Some of the components can be cut out by laser ablation or other material removal method, or not printed to begin with, to change data represented on the test strip. As explained below in detail, the amount of data that can be stored on each test strip can be maximized by arranging diodes in a bi-directional way, allowing one path to have 4 states: either shorted, opened, direction+ or direction−. More states can be added to one path by connecting diodes in series. Twice as many diodes give two more states such as direction++ and direction−− as explained below in detail. The number of diodes that can be connected in series may be limited, however, by the amount of voltage (or current) that a test meter can supply for DC excitation.

The principles of the present disclosure can be applied to test strips used with any diagnosis and monitoring system that would benefit from co-located information. The principles can be used in applications where inexpensive, high-volume memory produced using a reel-to-reel process (e.g., disposable memory and labels) is desired, and where the applications include electrical connections capable of supplying voltages and reading currents or vice versa.

Throughout the disclosure, diodes and resistors are used only as examples of active and passive components. Other components may be used instead or in addition. For example, the diodes and/or resistors can be implemented using Schottky-diodes, transistors such as bipolar junction transistors (BJTs), field-effect-transistors (FETs), and so on. Further supplying excitation and measuring response includes (i) supplying voltage and measuring current or (ii) supplying current and measuring voltage.

Figure 1:
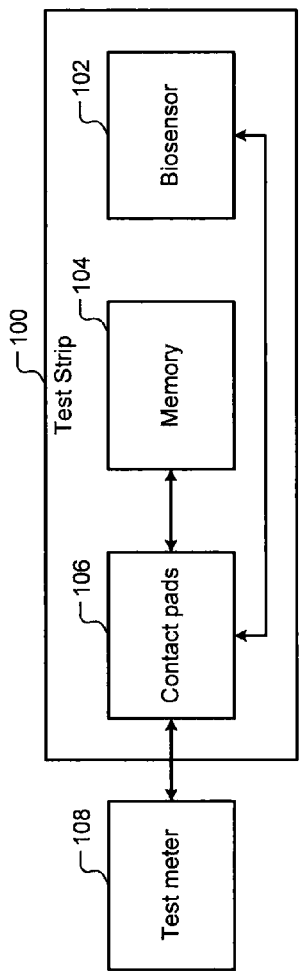
FIG. 1 is a functional block diagram of a test strip for analyzing a biological fluid using a test meter.

Referring now to FIG. 1, an example block diagram of a test strip 100 is shown. The test strip 100 includes a biosensor 102, memory 104, and contact pads 106. The biosensor 102 senses a sample of a biological fluid such as blood. The memory 104 includes information such as calibration data of a reagent used to analyze the sample, expiration date of the test strip 100, models of test meters with which the test strip 100 is compatible, and so on.

The contact pads 106 connect to corresponding contact pads of a test meter 108 when the test strip 100 is inserted into a port or a connector of the test meter 108. The contact pads 106 may include a first set of contact pads that connect to the biosensor 102 (typically called measurement contact pads) and a second set of contact pads that connect to the memory 104 (typically called information contact pads). In some implementations, the biosensor 102 and the memory 104 may share one or more of the contact pads 106. The test meter 108 reads the memory 104 and the biosensor 102 by applying voltages to the contact pads 106 as explained below in detail. The test meter 108 analyzes the information read from the memory 104 and the biosensor 102 and generates an analysis of the biological fluid.

Figure 9A:
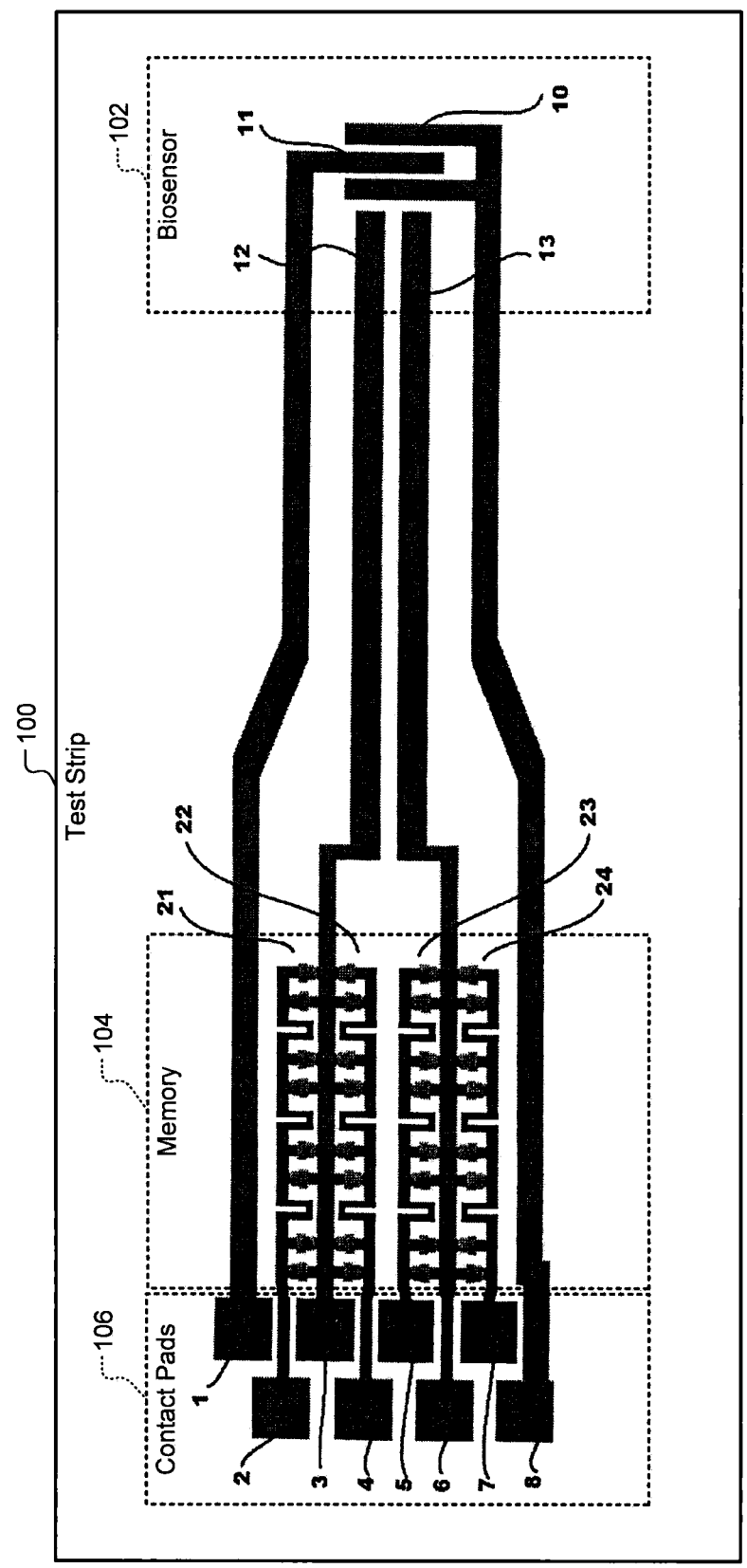
FIG. 9A depicts an example layout of a test strip.

An example of the biosensor 102 is shown in FIG. 9A, which depicts an example of a physical layout of the test strip 100. For example, the biosensor 102 can include two conductors, which are printed on the test strip 100 as shown in FIG. 9A, and a reagent deposited on the test strip 102, which reacts with a sample of a biological fluid deposited at or near the ends of the two conductors. The biosensor 102 communicates with two of the contact pads 106. In use, a sample of a biological fluid (e.g., a drop of blood) is deposited at or near the biosensor 102. The reagent deposited on the test strip 100 reacts with the biological fluid, which alters the electrical properties (e.g., resistance) of the biosensor 102. The test meter 108 applies a voltage to the contact pads that communicate with the biosensor 102, measures current, and determines a concentration level of an analyte (e.g., glucose) in the biological fluid.

Alternatively, the test meter 108 can inject current through one of a pair of contact pads and measure voltage across the pair of contact pads. Further, the test meter 108 can reverse the polarity of the voltage applied across contact pads and measure current. Alternatively, the test meter 108 can reverse the direction of the current injected by injecting the current through the other contact pad in the pair of contact pads and measure voltage across the pair of contact pads.

The principles of the present disclosure can be used in conjunction with other types of biosensors. Further, the principles of the present disclosure can be applied to test strips available from companies including Roche Diagnostics Operations, Inc.; Abbott Diabetes Care, Inc.; Bayer Healthcare LLC; and so on.

Initially, various memory architectures that can be printed on tests strips are shown and described below with reference to FIGS. 2A-8C. Subsequently, an example of a layout of the memory strip 100 that comports with the block diagram shown in FIG. 1 and that depicts the biosensor 102, the memory 104, and the contact pads 106 is shown in FIGS. 9A and 9C.

Figure 2A:
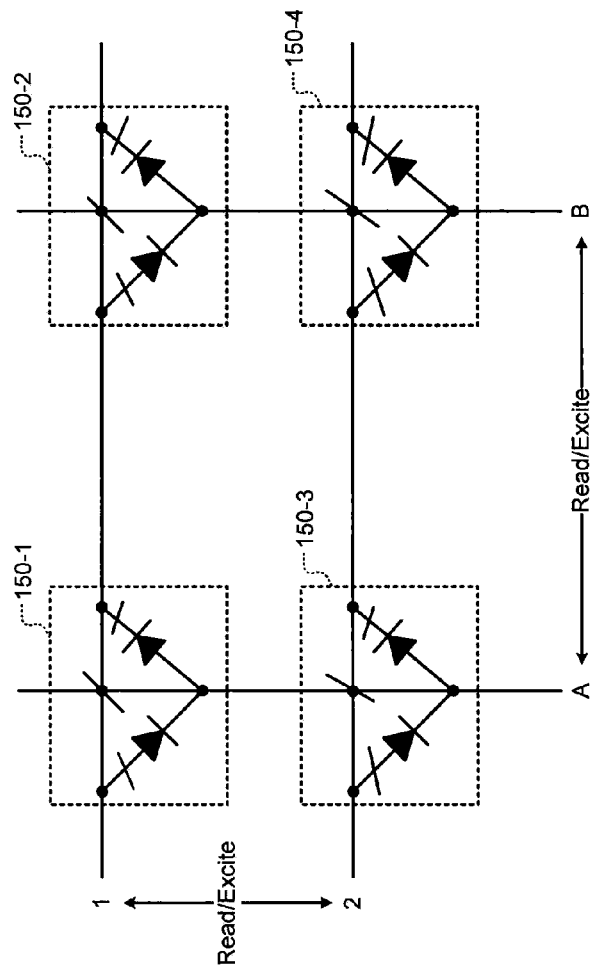
FIG. 2A is a schematic of a memory architecture including an arrangement of diodes and short circuits that can be used to represent data.

Referring now to FIGS. 2A-2D, examples of memory architectures that use diodes and corresponding logic tables are shown. In FIG. 2A, a memory architecture that includes a 2×2 matrix of diode nodes and that requires four contact pads (labeled 1, 2, A, and B) is shown. In FIG. 2B, a memory architecture that includes three serial diode nodes connected across two contact pads (labeled 1 and A) is shown.

A diode node includes two diodes connected in parallel across a short circuit. In a diode node, an anode of a first diode and a cathode of a second diode are connected to a first end of the short circuit, and the anode of the second diode and the cathode of the first diode are connected to a second end of the short circuit. In FIG. 2A, diode nodes are identified by reference numerals 150-1, 150-2, 150-3, and 150-4. In FIG. 2B, diode nodes are identified by reference numerals 160-1, 160-2, and 160-3.

In both memory architectures, memory or unique states are set by making a combination of cuts, which are represented in the figures by slash marks. Cuts to each node are either made on the short, the diode of one polarity, and/or the diode of the other polarity resulting in 5 states per node: Open, Short, +Polarity, −Polarity, or +/−Polarity. The states are read by applying a voltage higher than a forward voltage ($V_f$) of the diodes in series to the contact pair(s) and reading the current at the contact pair(s) with each possible polarity. For example, in FIG. 2A, a voltage higher than $2 \times V_f$ must be applied and the resulting current measured in one polarity. For example, in FIG. 2B, a voltage higher than $3 \times V_f$ must be applied and the resulting current measured in one polarity and then the other to capture all of the states. Alternative methods can be used to read the state of the memory. For example, a current can be applied, and the resulting voltage can be read.

In general, a voltage of first polarity is initially applied across a pair of contacts, and current is measured. For example, in FIG. 2A, a positive voltage is applied to contact pad 1, and a negative voltage is applied to contact pad 2. Subsequently, the polarity of the voltage is reversed, the voltage with reversed polarity is applied to the pair of contacts, and current is measured. For example, in FIG. 2A, the positive voltage is applied to contact pad 2, and the negative voltage is applied to contact pad 1. The process is repeated across each pair of contacts. For example, in FIG. 2A, the process is repeated across the contact pads A and B.

In FIG. 2A, each diode node has 5 possible states. A table shown in FIG. 2C shows all the states for the memory architecture shown in FIG. 2A based on combinations of cuts made. In the table, cut IDs 1 through 12 correspond to the cuts shown in FIG. 2A when the cuts are viewed from left to right, top to bottom. The cuts are not numbered in FIG. 2A to avoid cluttering.

In FIG. 2C, the table demonstrates that there are 4 unique states and 1 dependent state per diode node. The dependent state is related to the short circuit element. The short circuit element must be cut for other states to become active on adjacent nodes. Therefore, the estimated total number of states possible in this example is $4^4+4=260$ or just over 8 bits since $2^8=256$. While the 4 shorts provide only 4 extra states, the 4 shorts also provide a feature in each diode node that allows the node to be bypassed if not cut, which may be useful in more complex embodiments with many more diode nodes.

In FIG. 2B, each diode node has 5 possible states. A table shown in FIG. 2D shows all the states for the memory architecture shown in FIG. 2B based on combinations of cuts made. In the table, cut IDs 1 through 9 correspond to the cuts shown in FIG. 2B when the cuts are viewed from left to right, top to bottom. The cuts are not numbered in FIG. 2B to avoid cluttering.

In FIG. 2D, the table demonstrates that there are 5 unique states and 1 dependent state per diode node. The dependent state is related to the short circuit element. The short circuit element must be cut for other states to become active on each diode node. Therefore, the estimated total number of states provided in this example is $(3 \times 5)+3=18$ or just over 4 bits since $2^4=16$. While the 3 shorts provide only 3 extra states, the 3 shorts also provide a feature in each diode node that allows the diode node to be bypassed if not cut, which may be useful in more complex embodiments with many more diode nodes.

The diode nodes can be arranged in many different serial and/or parallel combinations to yield additional memory architectures with more memory capacity. Applying an excitation voltage to the diode nodes and measuring current in a bipolar method provide flexibility in designing the test strip 100. Examples of additional memory architectures are provided below.

Referring now to FIGS. 3A and 3B, an example of a memory architecture that uses three contact pads (labeled E1, E2, and E3) and a parallel, "ladder" type architecture is shown. In FIGS. 3A and 3B, the ladder structure includes a plurality of rungs 170-1, 170-2, and so on (collectively rungs 170). Each of the rungs includes two diode nodes. In FIG. 3A, additional diode nodes 180-1, 180-2, and so on (collectively additional diode nodes 180) are connected along a conducting path extending from the second contact pad (labeled E2). In some implementations, instead of the additional diode nodes 180, resistors (not shown) may be connected along the conducting path extending from the second contact pad (labeled E2). In FIG. 3B, the additional diode nodes 180 are not connected along the conducting path extending from the second contact pad (labeled E2).

In FIGS. 3A and 3B, while cuts are omitted for simplicity, each diode node can be cut in 3 places as shown and described previously. Each diode node has 5 possible states as described previously. The number of rungs 170 is shown to be expandable as an example of the flexibility of design provided by the present disclosure. More rungs 170 in the "ladder" can be added. The number of rungs 170 is limited by space on the test strip 100 and excitation/read capabilities of the test meter 108. Readings/Excitation can occur on 3 contact pad pairs (labeled E1, E2, and E3) as shown. Two of the three contact pads can be used for other functions on the test strip 100 such as sample dose detection if none of the rungs is shorted.

Generally, the number of states in the "ladder" architecture shown in FIG. 3A is estimated as at least $(5 \times 3+3) \times$Number of Rungs (i.e., $18 \times$Number of Rungs). For example, a ladder with 10 rungs can have at least 180 states or over 7 bits since $2^7=128$. Logic tables for the memory architectures shown in FIGS. 3A and 3B would depend on the number of rungs 170 selected and resolution of the test meter 108 and are therefore omitted.

The ladder architectures can be expanded to include resistors. For example, resistors can be used to replace the diode nodes connected along the conducting path extending from the second contact pad, allowing tuning of expected current readings and ranges. Additional configurations using resistors are possible. Examples of memory architectures using resistors are provided below.

Figure 4E:
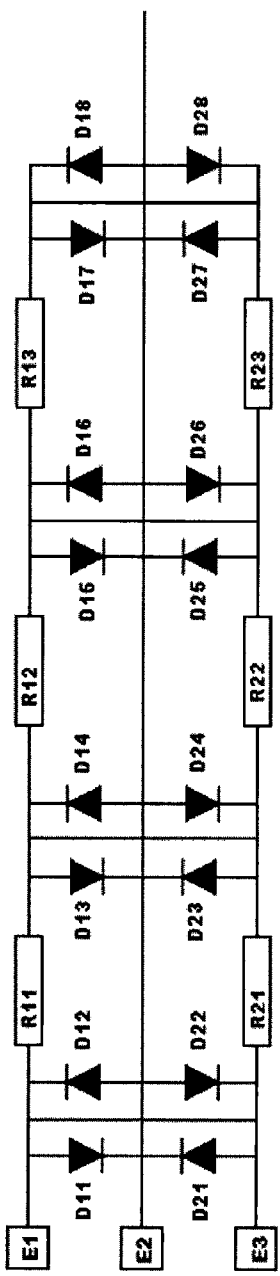
FIGS. 4E and 4F depict different combinations of the layout shown in FIG. 4A with two lines and four lines, respectively.

Referring now to FIGS. 4A-4E, a basic ladder structure, which forms the basis for the layouts of memory architectures of FIGS. 4 and 5, is shown. In FIG. 4A, a ladder structure representing one line of memory is shown. In the ladder structure, a cell includes a pair of diodes, one short, and one resistor. A first cell contains no resistor and may be interpreted as one resistor with a resistance value of 0 Ohms. Diodes labeled Dxx and shorts labeled Kx are considered active if there is an electrical connection via the diode or the short, from the conductor starting at contact E2, directly or via one or more of the resistors Rxx, to the contact E1.

Figure 4F:
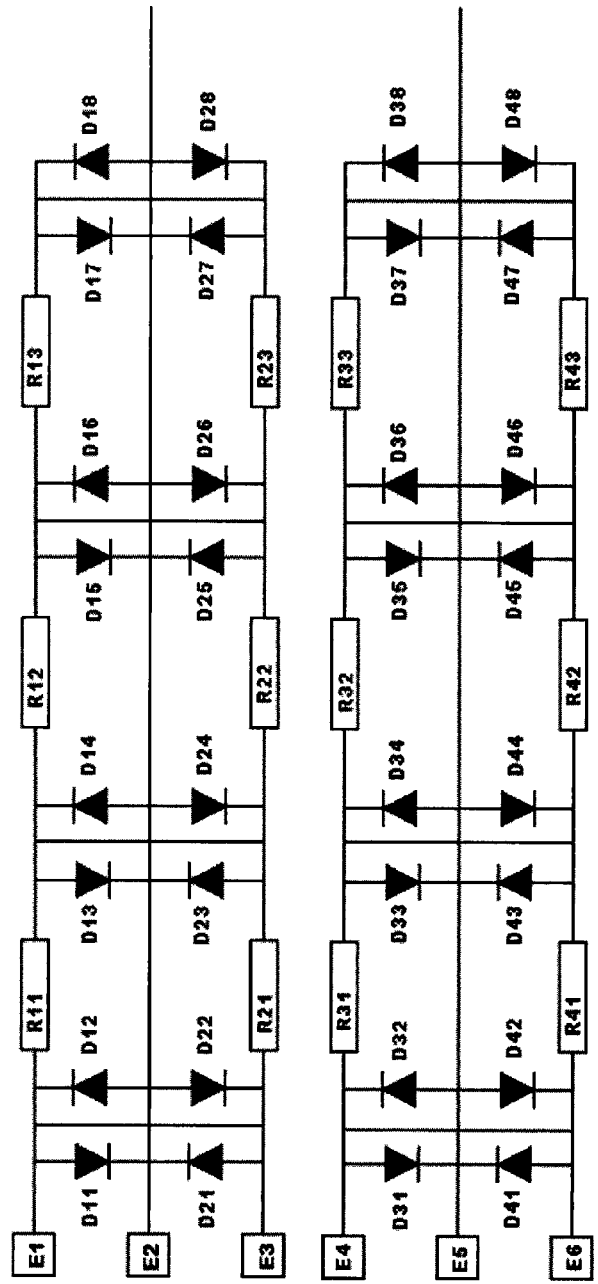

In FIG. 4B, if only one diode is active within one line of memory, 8 different states are possible, which represent 3 bits of information shown. In FIG. 4C, if one or two diodes are active within one line of memory, 36 different states are possible, which represent more than 5 bits of information. If one short is active within one line of memory, 4 different states are possible, which represent 2 bits of information. In FIG. 4D, if one short and one diode are active within one line of memory, 16 different are states possible, which represent 4 bits of information. Activating three or more elements within one line of memory will increase the number of different states. The number of usable states that will be distinguishable from each other, however, will be less due to manufacturing and measurement tolerances. For example, 53 different states are possible with zero to two active elements within one line of memory, which represent more than 5 bits of information. With manufacturing and measurement tolerances of +/−30%, however, only 32 of the 53 states can be distinguished from each other, which yield 5 bits of information. Tolerances of +/−10% yield 35 states that can be distinguished, which provide more than 5 bits of information, and so on. In FIGS. 4E and 4F, different combinations of the layout shown in FIG. 4A with two lines and four lines are shown, respectively.

Figure 4G:
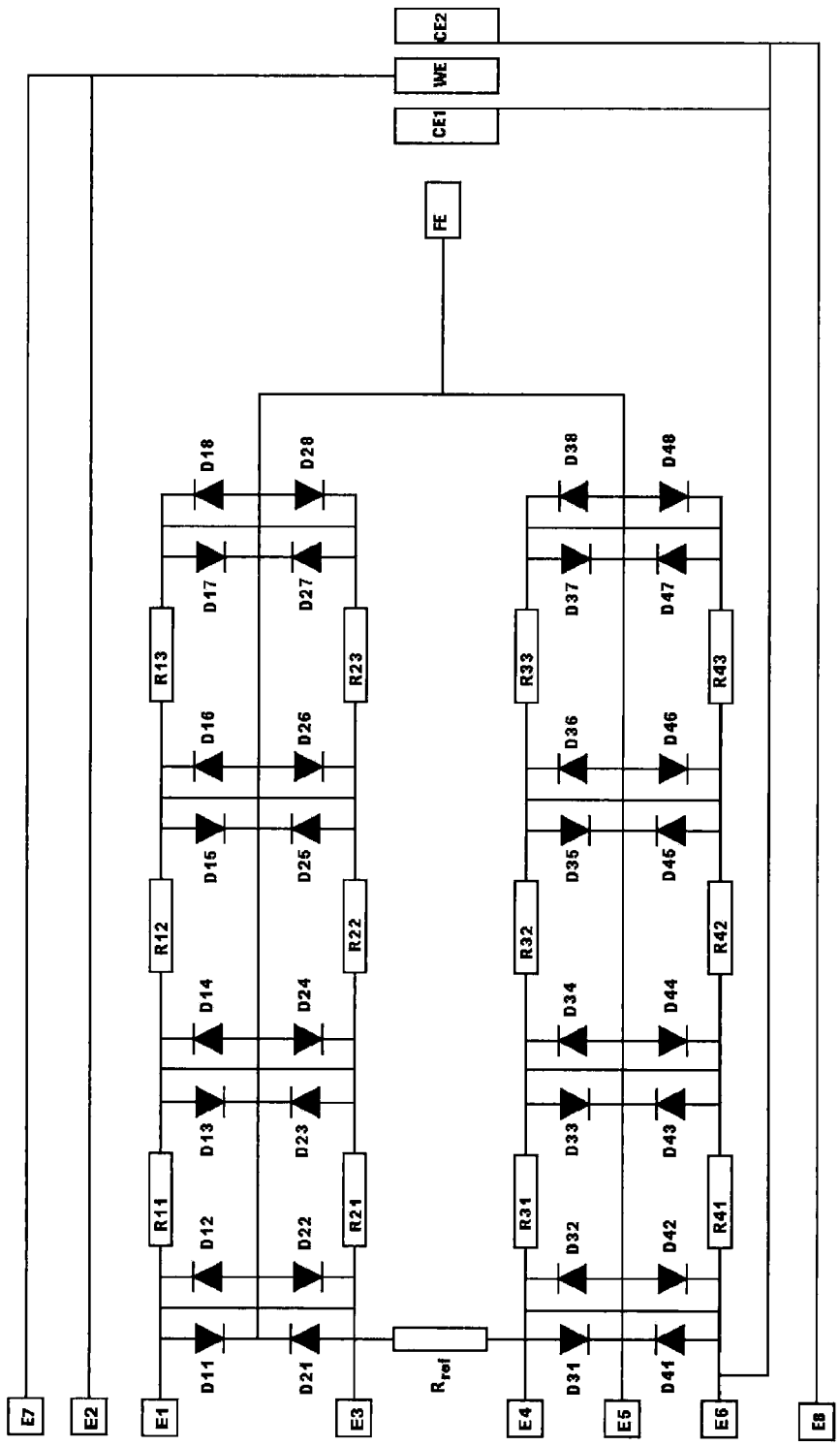
FIG. 4G depicts a schematic of a memory architecture including a reference resistor.
Figure 9B:
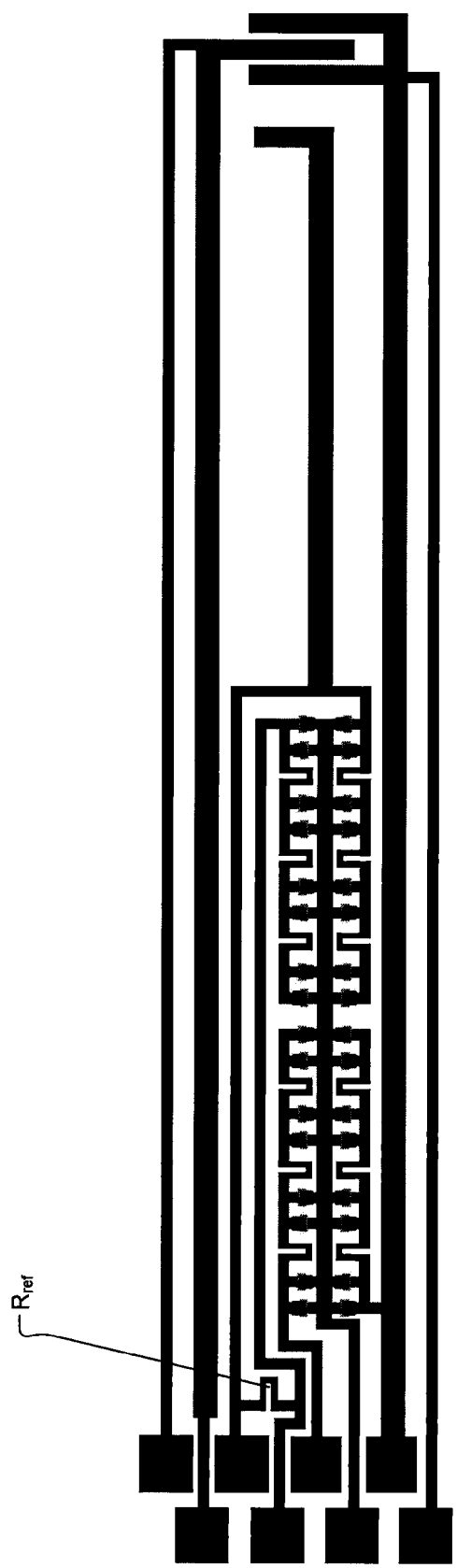
FIG. 9B depicts an example layout of a test strip including a reference resistor.

In FIG. 4G, a schematic of a memory architecture including a reference resistor $R_{ref}$ is shown. The reference resistor $R_{ref}$ is used to calibrate the system in order to supply the excitation that is compensated for temperature and resistor variations. The memory architecture uses multiple contact pads and provides relatively large memory per contact pad. An example of a physical layout of a test strip including the memory architecture is shown in FIG. 9B.

The test strip includes a Fill Electrode (FE), a Working Electrode (WE), and multiple Counter Electrodes (CE1 and CE2). The Fill Electrode is a sample sufficiency electrode and senses presence of biological fluid. An electrochemical reaction takes place on the surface of the working electrode, and the analyte is oxidized or reduced. The counter electrodes CE1 and CE2 are complimentary to the working electrode and receive excitation supplied to activate the electrochemical reaction to achieve the required oxidation or reduction. At least one of the electrode contact pads is shared by the memory architecture.

Figure 5A:
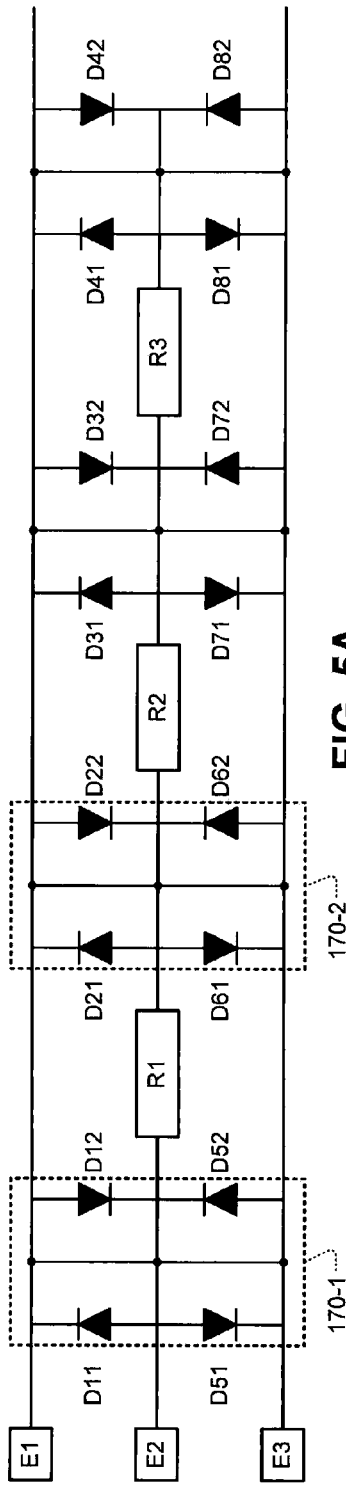
FIG. 5A is a schematic of a memory architecture including an arrangement of diodes, resistors, and short circuits that can be used to represent data on a test strip.

Referring now to FIGS. 5A-5D, examples of memory architectures using diodes and resistors are shown. In FIG. 5A, between each pair of adjacent rungs 170, resistors R1, R2, and so on are connected along the conducting path extending from the second contact pad (labeled E2). Resistors are not connected in conducting paths extending from first and third contact pads (labeled E1 and E3, respectively).

Figure 5B:
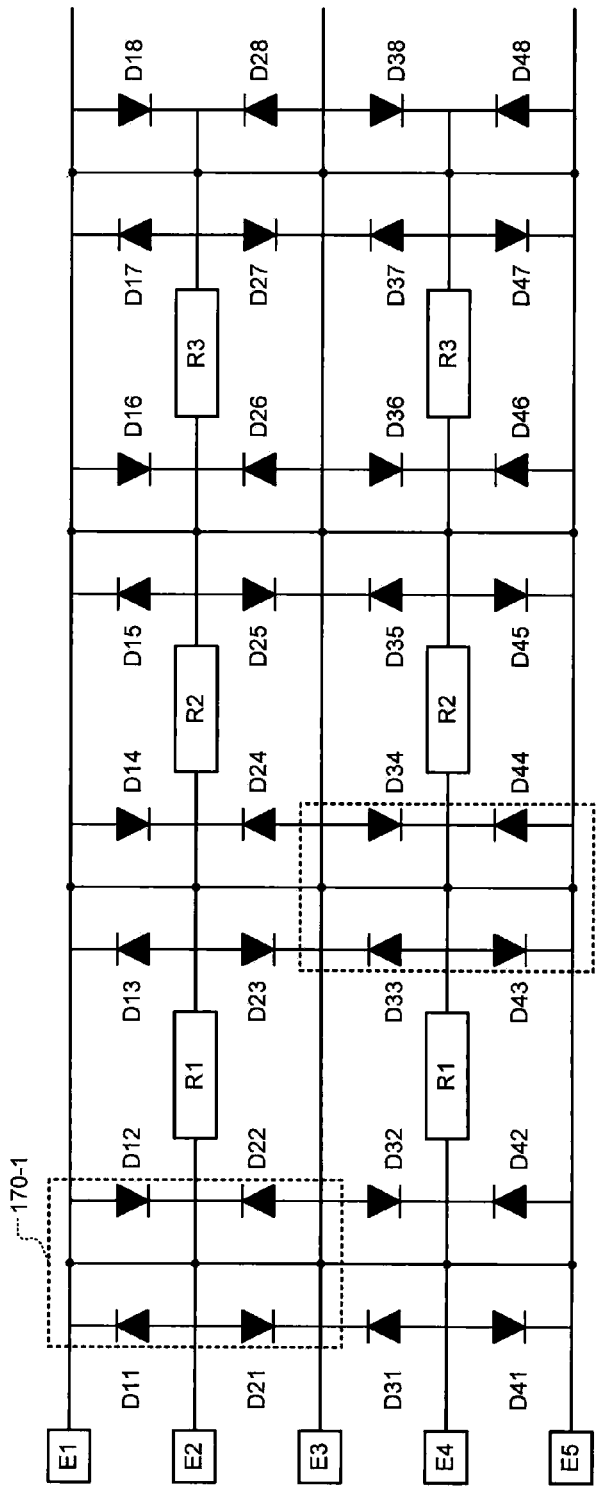
FIG. 5B is a schematic of a memory architecture including an arrangement of diodes, resistors, and short circuits that can be used to represent data on a test strip.

In FIG. 5B, memory capacity can be increased by adding diode nodes and resistors along conducting paths extending from additional contact pads as shown. While short circuits are shown in each diode node, the shorts may be omitted in some implementations. Again, cuts are omitted for simplicity of illustration, and can be incorporated as previously shown and described. Notations with the letter "E" denote contact pads throughout the disclosure.

Contact pads that are used to communicate with the biosensor 102 may also be shared to excite/read states of the memory architecture. Typically, however, the conducting path extending from the contact pad used to communicate with the biosensor 102 may not include a resistor. Accordingly, the conducting path extending from the shared contact pad may not include a resistor.

For example, in FIG. 5A, the conducting path extending from the second contact pad (Labeled E2) includes resistors and therefore can be used to read/excite states of the memory architecture but cannot be used to communicate with the biosensor 102. Conversely, conducting paths extending from the first and second contact pads (labeled E1 and E3) do not include resistors and therefore can be used to excite/read states of the memory architecture and to communicate with the biosensor 102.

In FIG. 5C, assuming that the diode nodes do not include shorts, depending on the cuts made, a table shows possible options for output resistances for one line and one polarity of the voltage applied, where a line is a conducting path between a pair of adjacent contact pads. For example, the memory architecture shown in FIG. 5A has two lines, and the memory architecture shown in FIG. 5B has four lines. The polarity is that of a DC voltage applied across a pair of adjacent contact pads of a line.

In the table shown in FIG. 5C, the options are numbered from 1 to 9. RDD denotes a forward resistance of a diode. RDS denotes a reverse resistance of a diode. Mathematically, options 7 and 8 result in identical resistances and thus indistinguishable states. Options 6 and 9 can be reliably distinguished if manufacturing tolerances of the resistors are strict (e.g., less than 10%). Consequently, option 7 can result in distinguishable states or output values in one line at one polarity. Accordingly, depending on the number of lines and cuts, memory architectures such as those shown in FIGS. 5A and 5B (assuming diode nodes without shorts) can yield different memory capacities shown in FIG. 5D.

The layouts shown in FIGS. 4E and 4F differ from the layouts shown in FIGS. 5A and 5B in that in FIGS. 4E and 4F, there is electrical independence of the possible states in adjacent lines from each other. For example, unlike in FIGS. 4E and 4F, in FIG. 5A, two active diodes (e.g., D52 and D61) from line 2 (i.e., a line between contacts E2 and E3) can act as a parallel resistor to R1 while a meter is reading a combination with the resistor R1. This parallel resistor will modify the output and therefor possibly adulterate the read out information. Accordingly, FIG. 5D indicates the number of useful states and bits being less than the total number of possible states and bits.

Figure 6:
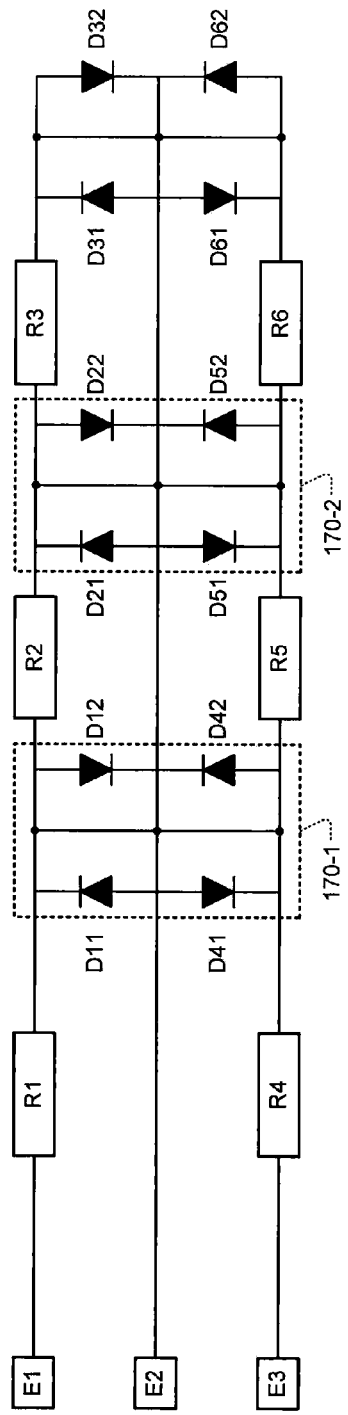
FIG. 6 is a schematic of a memory architecture including an arrangement of diodes, resistors, and short circuits that can be used to represent data on a test strip.

Referring now to FIG. 6, another example of memory architecture using resistors is shown. While short circuits are shown in each diode node, the shorts may be omitted in some implementations. In the example shown, the resistors are not used in the conducting path extending from the second contact pad (labeled E2). Rather, the resistors are used in the conducting paths extending from the first and second contact pads (labeled E1 and E3, respectively) as shown.

Resistors R1 through R6 may be identical. Alternatively, resistors may increase in value from R1 through R3 and from R4 though R6. Two diodes connected back-to-back are allocated to each resistor. For example, diodes D11 and D12 are allocated to resistor R1; diodes D21 and D22 are allocated to resistor R2; and so on. A unit comprising two diodes connected back-to-back and the resistor allocated to the two diodes may be referred to as a cell.

To read out the memory, the test strip is inserted into the test meter having matching contacts. The test meter applies DC voltage across contact pads E1 and E2, measures the resistance across the contact pads E1 and E2. The resistance can have seven different values depending on the position of an active diode in the conducting direction: no contact, $(R1+R_{diodeforward})$, $(R1+R_{diodereverse})$, $(R1+R2+R_{diodeforward})$, $(R1+R2+R_{diodereverse})$, $(R1+R2+R3+R_{diodeforward})$, $(R1+R2+R3+R_{diodereverse})$. Subsequently, the test meter applies the DC voltage across contact pads E1 and E2 with the polarity of the DC voltage reversed. Again, seven resistance values are possible.

Note that each physical configuration is represented by two resistance values, one for each polarity of the DC voltage. Therefore, the measurement yields a possible differentiation of 7 combinations or states. The information can be read out similarly via contact pads E2 and E3. Again, there are 7 possible combinations. Accordingly, the memory architecture shown in FIG. 6 comprises 49 combinations, which correspond to more than 5 bits. To increase the memory capacity, more lines can be added. If the resistors are manufactured with precision, more cells can be added to a line.

Thus, for 4 cells per line, the memory per line is more than 3 bit; for 5 cells per line, the memory per line is more than 3 bit; and so on.

If the resistors and diodes can be manufactured sufficiently precisely, more than one diode can be switched to active state per line. For lines comprising 3 cells, a potential memory capacity of 22 states is possible with up to 2 active diodes per line, and a potential memory capacity of 42 states is possible with up to 3 active diodes per line. For lines comprising 4 cells, a potential memory capacity of 37 states is possible with up to 2 active diodes per line, and a potential memory capacity of 90 states is possible with up to 3 active diodes per line. The principle can be extended to obtain a desired memory capacity. The extension may be limited due to inaccuracy of resistors caused by manufacturing process. In addition, more lines also require more contact pads and more area on the test strip. To minimize contact pads, some contact pads such as contact pads used for filling level control can also be used for communicating with the memory. Risk of interference in sharing contact pads can be low since memory content is read out only once before wetting the test strip with a sample.

Instead of, or in addition to, using resistors, scaled-area diodes may be used. For example, junction areas of the diodes may be scaled to represent a binary code. A diode's forward current is proportional to a junction area of the diode's PN junction. Therefore, diodes with scaled junction areas can produce currents that are proportional to their junction areas when driven by the same voltage. Several diodes that are connected in parallel and are scaled in junction area according to a binary sequence (X1, X2, X4, X8, etc.) should result in a current that represents the sum of the areas of the connected diodes when a voltage is applied across these diodes in parallel.

Figure 7D:
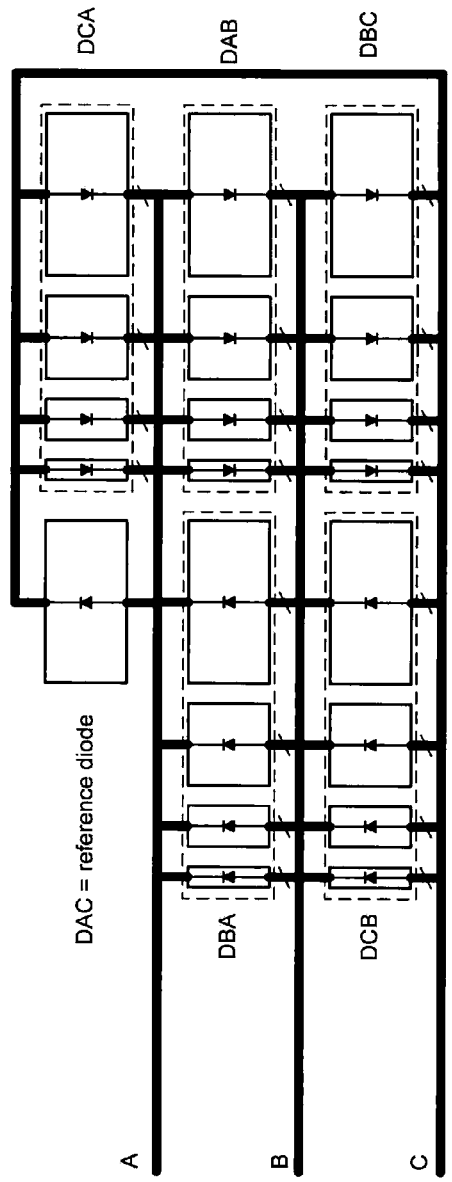
FIG. 7D depicts an example of a layout of the diodes shown in FIG. 7A.
Figure 7A:
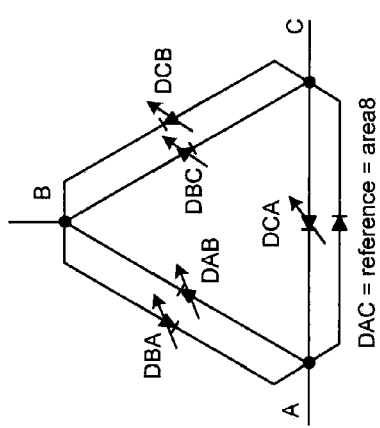
FIG. 7A is a schematic of a memory architecture including an arrangement of diodes that can be used to represent data on a test strip, where junction areas of the diodes are scaled to a binary code.
Figure 7B:
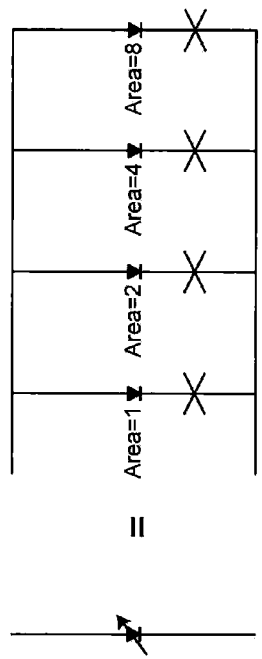
FIG. 7B depicts diodes connected in parallel across a pair of contacts of a test strip, where junction areas of the diodes are scaled to a binary code.
Figure 7C:
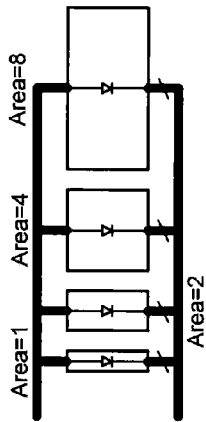
FIG. 7C depicts a layout of diodes shown in FIG. 7B.

Referring now to FIGS. 7A-7D, an example of a memory architecture including scaled-area diodes is shown. In FIG. 7A, the memory architecture includes 6 legs connected between 3 contact pads labeled A, B and C. Five of the six legs include diodes in parallel that are scaled in junction area by X1, X2, X4, X8 (i.e., a binary code) as shown in FIGS. 7B and 7C. The $6^{th}$ leg includes a reference diode that can have an X8 junction area or other junction area scaling depending upon implementation. The $6^{th}$ leg is needed to calibrate the system in order to generate the proper excitation voltage that is compensated for temperature and diode variations. The reference diode may also be used for calibration purposes in other memory architectures disclosed herein.

The total number of diodes is (5×4)+1 reference=21 diodes. The reference diode has a relative area of 8, resulting in a current that is 8/15 of full scale at the output. Other choices are possible, including X1+X2+X4+X8=X15 which would yield the full scale output. Each leg is excited by a voltage source, and the resulting diode current is read. The X8 reference diode is read first and the voltage source is adjusted until a reading of 8/15 of full scale is obtained at the output. The current through each parallel diode should scale with its junction area. Thus, the resulting current should take on relative values of 0, 1, 2, 3, . . . , and 15 depending upon which diodes have been cut out of the circuit by laser ablation cuts. Each of the 5 legs yields 4 bits (16 valid combinations) for a total of 20 bits. An example of a physical layout of the entire memory architecture is shown in FIG. 7D. Other layouts are possible. FIG. 7D demonstrates that no vias are required since all components and traces are on the same layer.

Figure 8B:
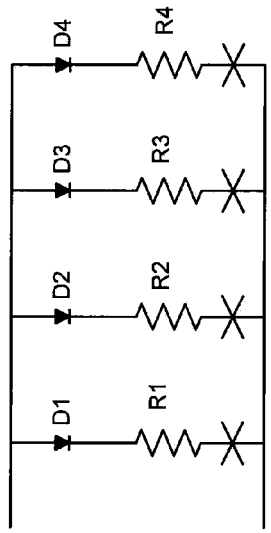
FIGS. 8B and 8C depict different arrangements of diodes and resistors.
Figure 8C:
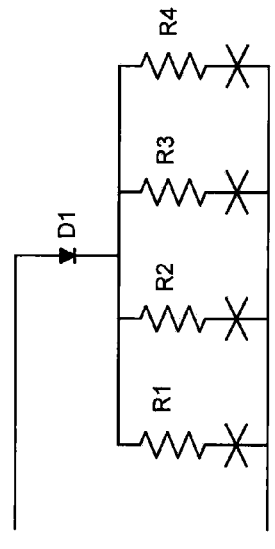
Figure 8A:
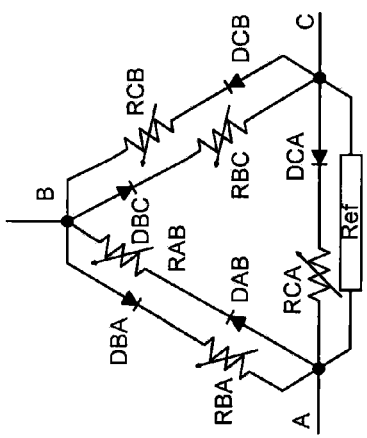
FIG. 8A is a schematic of a memory architecture including an arrangement of diodes and resistors that can be used to represent data on a test strip, where junction areas of the diodes and values of the resistors are scaled to a binary code.
Figure 9C:
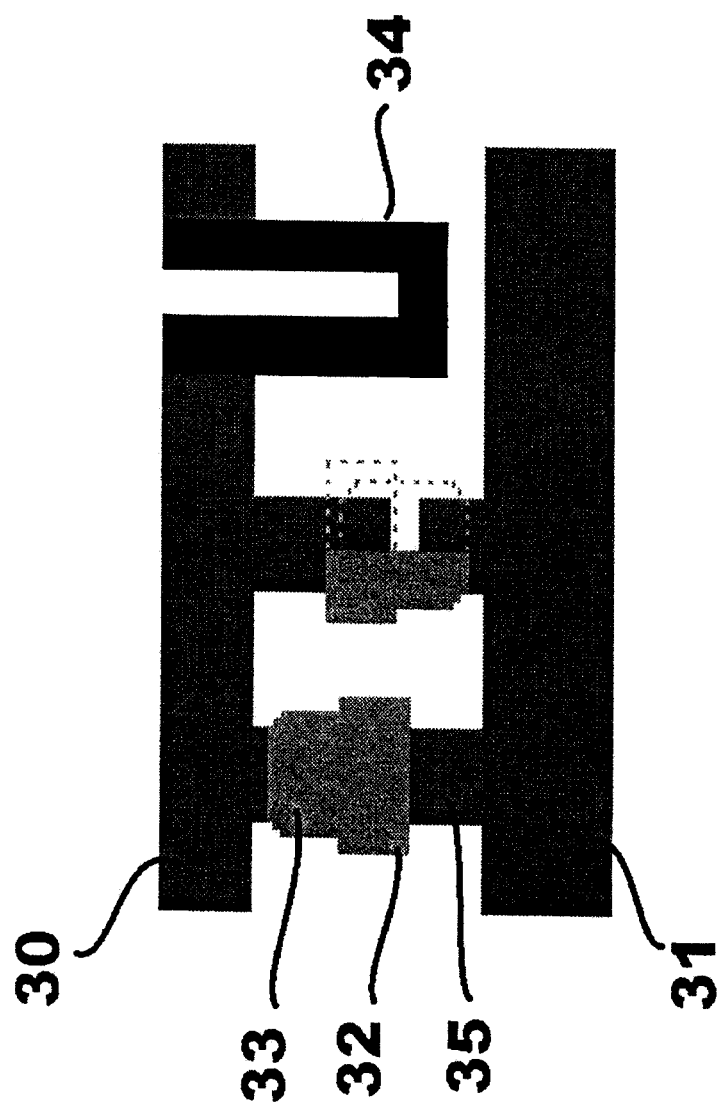
FIG. 9C depicts an example of an individual memory cell comprising 2 diodes and a resistor.

Referring now to FIGS. 8A-8C, diodes and resistors that are scaled to a binary code can be combined in a memory architecture. In FIG. 8A, an example of a memory architecture including 6 legs connected to 3 contact pads (labeled A, B, and C) is shown. One of the 6 legs is used as a reference. In one implementation shown in FIG. 8B, all diodes are identical (i.e., D1=D2=D3=D4), and values of resistors vary according to a binary code (e.g., R1=2R2=4R3=8R4). In another implementation shown in FIG. 8C, a single diode is used instead of multiple diodes, and values of resistors vary according to a binary code.

In a variation of the implementation shown in FIG. 8B, both the diodes and the resistors can be scaled according to the binary code (e.g., D1=X1 area, D2=X2 area, D3=X4 area, and D4=X8 area, and R1=8R, R2=4R, R3=2R, and R4=R). The basic scheme described with reference to FIGS. 6A-6C can be used, which involves driving the legs with a calibrated voltage and measuring the resulting current. Scaling both the resistors and the diodes can cause the current to scale linearly with the binary code. The reference network can be a X8 area diode in series with R.

The use of binary-scaled resistors can help compensate for non-ideal properties of diodes, which occur due to process variations. For example, actual diode currents may depart from expected diode currents due to variations in their scaled areas caused by process variations across the test strip. The variations, if large enough, can cause problems with the memory architectures. Adding resistors in series with the diodes increases complexity of the structure and requires more voltage to read states, but also reduces current variations and improves accuracy.

Referring now to FIGS. 9A and 9C, an example layout of the test strip 100 is shown. In FIG. 9A, the test strip 100 includes eight contact pads identified by reference numerals 1 through 8. Reference numerals 10 and 11 denote measuring electrodes. Reference numerals 12 and 13 denote filling level electrodes. Reference numerals 21 through 24 denote memory lines.

In FIG. 9C, an individual memory cell comprising 2 diodes and a resistor is shown. Reference numerals 30 and 31 denote conducting paths. Reference numeral 32 denotes semiconductor material. Reference numeral 34 denotes a resistor. Reference numeral 35 denotes a position where the conducting path may be cut (i.e., opened). Reference numeral 33 denotes a counter electrode. FIG. 9C shows an example of a test strip that includes a reference resistor $R_{ref}$ and that implements the schematic shown in FIG. 4G.

In manufacturing of test strips, conducting paths, contact pads, and electrodes can be manufactured in many ways. For example, gold can be sputtered onto foil and structured by laser ablation. Copper can similarly be sputtered onto PET foil and subsequently structured by laser. The structuring of copper can also be performed using photolithography. The conducting paths, contact pads, and electrodes can also be printed using silver paste, copper paste, carbon paste, or PEDOT:PSS-paste. The metal transfer process can also be used to deposit (i.e., to print) copper or another suitable metal such as Ag, Au, Pt, Ni, Al, Zn, Sn, Fe, Mn, or Ti in a confined space. It is also possible to print organic transistors instead of diode structures, where the base and collector are directly connected together or via a resistor. Such a transistor functions as a diode.

The conducting paths and the associated contact pads can be formed in one process step together with the electrode structures, or in two or more process steps by laser ablation, metal transfer or by printing with one or more than one different inks, for example. This processes usually take place on a continuous tape in a roll-to-roll process. Subsequently, resistors are printed at the intended positions using screen printing, flexo printing, gravure printing, laser transfer printing or inkjet printing. Gaps of different widths in the conducting paths are printed over with resistor paste. Diodes comprising organic semiconductors are printed from a solution or dispersion in at least two subsequent steps. Where necessary a post-treatment process like drying or annealing can be performed.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims.

For purposes of clarity, the same reference numbers will be used in the drawings to identify similar elements. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

What is claimed is:

1. A test strip for analyzing a biological fluid using a test meter, the test strip comprising:
    a biosensor configured to sense the biological fluid, wherein the biosensor comprises a pair of conductors printed on the test strip to communicate with the test meter and a reagent deposited on the test strip to react with the biological fluid;
    first, second, and third contacts configured to communicate with the test meter, wherein at least two of the first, second, and third contacts are configured to communicate with the pair of conductors of the biosensor;
    first, second, and third conductors connected to the first, second, and third contacts, respectively, wherein at least two of the first, second, and third conductors are included in the pair of conductors of the biosensor;
    first and second diodes each having a first end connected to the first conductor and a second end connected to the second conductor at a first node so that the first diode is connected to the second diode in opposing polarity;
    third and fourth diodes each having a first end connected to the second conductor at the first node and a second end connected to the third conductor so that the third diode is connected to the fourth diode in opposing polarity;
    a first short circuit having (i) a first end connected to the first ends of the first and second diodes and (ii) a second end connected to the second ends of the first and second diodes; and
    a second short circuit having (i) a first end connected to the first ends of the third and fourth diodes and (ii) a second end connected to the second ends of the third and fourth diodes,
    wherein the test strip is configured to store data based on a first number of connections severed between (i) the first through fourth diodes and the first through third conductors and (ii) the first and second ends of the first and second short circuits.

2. The test strip of claim 1, further comprising:
    fifth and sixth diodes each having a first end connected to the first conductor and a second end connected to the second conductor at a second node so that the fifth diode is connected to the sixth diode in opposing polarity;
    seventh and eighth diodes each having a first end connected to the second conductor at the second node and a second end connected to the third conductor so that the seventh diode is connected to the eighth diode in opposing polarity;
    a third short circuit having (i) a first end connected to the first ends of the fifth and sixth diodes and (ii) a second end connected to the second ends of the fifth and sixth diodes; and
    a fourth short circuit having (i) a first end connected to the first ends of the seventh and eighth diodes and (ii) a second end connected to the second ends of the seventh and eighth diodes,
    wherein the test strip is configured to store data based on a second number of connections severed between (i) the first through eighth diodes and the first through third conductors and (ii) the first and second ends of the first through fourth short circuits.

3. The test strip of claim 2, further comprising:
    ninth and tenth diodes each having a first end connected to the first node and a second end connected to the second node so that the ninth diode is connected to the tenth diode in opposing polarity; and
    a fifth short circuit having (i) a first end connected to the first node and (ii) a second end connected to the second node,
    wherein the test strip is configured to store data based on a third number of connections severed between (i) the first through tenth diodes and the first through third conductors and (ii) the first and second ends of the first through fifth short circuits.

4. The test strip of claim 2, further comprising:
    a resistance having a first end connected to the first node and a second end connected to the second node,
    wherein the test strip is configured to store data based on a third number of connections severed between (i) the first through eighth diodes and the first through third conductors and (ii) the first and second ends of the first through fourth short circuits.

5. A system comprising:
    the test strip of claim 1; and
    the test meter,
    wherein the test meter is configured to sense the data by
        supplying excitation across the first and second contacts and measuring response between the first and second contacts,
        supplying excitation across the second and third contacts and measuring response between the second and third contacts, and
        supplying excitation across the first and third contacts and measuring response between the first and third contacts.

6. The system of claim 5, wherein the data include at least one of (i) information to calibrate the test meter and (ii) information about the test strip.

7. The system of claim 5, wherein when a sample of the biological fluid is placed on the test strip at or near the ends of the pair of conductors of the biosensor, the test meter is configured to determine a concentration level of an analyte in the biological fluid by sensing a change in an electrical property of the biosensor.

8. A test strip for analyzing a biological fluid using a test meter, the test strip comprising:
    a biosensor configured to sense the biological fluid, wherein the biosensor comprises a pair of conductors printed on the test strip to communicate with the test meter and a reagent deposited on the test strip to react with the biological fluid;

first, second, and third contacts configured to communicate with the test meter, wherein at least one of the first and third contacts are configured to communicate with the pair of conductors of the biosensor;

first, second, and third conductors connected to the first, second, and third contacts, respectively, wherein at least one of the first and third conductors are included in the pair of conductors of the biosensor;

first and second diodes each having a first end connected to the first conductor and a second end connected to the second conductor at a first node so that the first diode is connected to the second diode in opposing polarity;

third and fourth diodes each having a first end connected to the second conductor at the first node and a second end connected to the third conductor so that the third diode is connected to the fourth diode in opposing polarity;

a resistance having a first end connected to the first node, and a second end;

fifth and sixth diodes each having a first end connected to the first conductor and a second end connected to the second end of the resistance at a second node so that the fifth diode is connected to the sixth diode in opposing polarity; and seventh and eighth diodes each having a first end connected to the second node and a second end connected to the third conductor so that the seventh diode is connected to the eighth diode in opposing polarity, wherein the test strip is configured to store data based on a first number of connections severed between the first through eighth diodes and the first through third conductors.

9. A system comprising:
the test strip of claim 8; and
the test meter,
wherein the test meter is configured to sense the data by
supplying excitation across the first and second contacts and measuring response between the first and second contacts,
supplying excitation across the second and third contacts and measuring response between the second and third contacts, and
supplying excitation across the first and third contacts and measuring response between the first and third contacts.

10. The system of claim 9, wherein the data include at least one of (i) information to calibrate the test meter and (ii) information about the test strip.

11. The system of claim 9, wherein when a sample of the biological fluid is placed on the test strip at or near the ends of the pair of conductors of the biosensor, the test meter is configured to determine a concentration level of an analyte in the biological fluid by sensing a change in an electrical property of the biosensor.

12. A test strip for analyzing a biological fluid using a test meter, the test strip comprising:
a biosensor configured to sense the biological fluid, wherein the biosensor comprises a pair of conductors printed on the test strip to communicate with the test meter and a reagent deposited on the test strip to react with the biological fluid;
first and second contacts configured to communicate with the test meter;
first and second conductors connected to the first and second contacts, respectively;
a first resistance having a first end connected to the first contact, and a second end;
first and second diodes each having a first end connected to the second end of the first resistance and a second end connected to the second conductor at a first node so that the first diode is connected to the second diode in opposing polarity;
a second resistance having a first end connected to the second end of the first resistance, and a second end; and
third and fourth diodes each having a first end connected to the second end of the second resistance and a second end connected to the second conductor at a second node so that the third diode is connected to the fourth diode in opposing polarity,
wherein the test strip is configured to store data based on a first number of connections severed between the first through fourth diodes and the first and second conductors.

13. The test strip of claim 12, wherein the first resistance is equal to the second resistance.

14. The test strip of claim 12, wherein the second resistance is greater than the first resistance.

15. The test strip of claim 12, further comprising:
a third contact configured to communicate with the test meter;
a third conductor connected to the third contacts;
a third resistance having a first end connected to the third contact, and a second end;
fifth and sixth diodes each having a first end connected to the second end of the third resistance and a second end connected to the second conductor at the first node so that the fifth diode is connected to the sixth diode in opposing polarity;
a fourth resistance having a first end connected to the second end of the third resistance, and a second end; and
seventh and eighth diodes each having a first end connected to the second end of the fourth resistance and a second end connected to the second conductor at the second node so that the seventh diode is connected to the eighth diode in opposing polarity,
wherein the test strip is configured to store data based on a second number of connections severed between the first through eighth diodes and the first through third conductors.

16. The test strip of claim 15, wherein the first through fourth resistances are equal.

17. The test strip of claim 15, wherein the second resistance is greater than the first resistance, and wherein the fourth resistance is greater than the third resistance.

18. The test strip of claim 12, further comprising:
a first short circuit having (i) a first end connected to the first ends of the first and second diodes and (ii) a second end connected to the second ends of the first and second diodes; and
a second short circuit having (i) a first end connected to the first ends of the third and fourth diodes and (ii) a second end connected to the second ends of the third and fourth diodes,
wherein the test strip is configured to store data based on a second number of connections severed between (i) the first through fourth diodes and the first and second conductors and (ii) the first and second ends of the first and second short circuits.

19. The test strip of claim 15, further comprising:
a first short circuit having (i) a first end connected to the first ends of the first and second diodes and (ii) a second end connected to the second ends of the first and second diodes;

a second short circuit having (i) a first end connected to the first ends of the third and fourth diodes and (ii) a second end connected to the second ends of the third and fourth diodes;

a third short circuit having (i) a first end connected to the first ends of the fifth and sixth diodes and (ii) a second end connected to the second ends of the fifth and sixth diodes; and a fourth short circuit having (i) a first end connected to the first ends of the seventh and eighth diodes and (ii) a second end connected to the second ends of the seventh and eighth diodes, wherein the test strip is configured to store data based on a third number of connections severed between (i) the first through eighth diodes and the first through third conductors and (ii) the first and second ends of the first through fourth short circuits.

20. A system comprising:
the test strip of claim 15; and
the test meter,
wherein the test meter is configured to sense the data by
supplying excitation across the first and second contacts and measuring response between the first and second contacts,
supplying excitation across the second and third contacts and measuring response between the second and third contacts, and
supplying excitation across the first and third contacts and measuring response between the first and third contacts.

21. The system of claim 20, wherein the data include at least one of (i) information to calibrate the test meter and (ii) information about the test strip.

22. The system of claim 20, wherein the test meter is configured to communicate with the biosensor via the second contact.

23. A test strip for analyzing a biological fluid using a test meter, the test strip comprising:
a biosensor configured to sense the biological fluid, wherein the biosensor comprises a pair of conductors printed on the test strip to communicate with the test meter and a reagent deposited on the test strip to react with the biological fluid;
first and second contacts configured to communicate with the test meter;
first and second conductors connected to the first and second contacts, respectively, wherein at least one of the first and second conductors is different than the pair of conductors; and
a first plurality of diodes each having a first end connected to the first contact and a second end connected to the second contact,
wherein junction areas of the first plurality of diodes are scaled according to a binary code, and
wherein the test strip is configured to store data based on a first number of connections severed between the first plurality of diodes and the first and second conductors.

24. The test strip of claim 23, further comprising:
a second plurality of diodes each having a first end connected to the first contact and a second end connected to the second contact so that the first plurality of diodes is connected to the second plurality of diodes in opposing polarity,
wherein junction areas of the second plurality of diodes are scaled according to the binary code, and
wherein the test strip is configured to store data based on a second number of connections severed between the first and second pluralities of diodes and the first and second conductors.

25. A system comprising:
the test strip of claim 24; and
the test meter,
wherein the test meter is configured to
sense the data by supplying excitation across the first and second contacts and measuring response between the first and second contacts, and
communicate with the biosensor via at least one of the first and second contact, and
wherein the data include at least one of (i) information to calibrate the test meter and (ii) information about the test strip.

26. A test strip for analyzing a biological fluid using a test meter, the test strip comprising:
a biosensor configured to sense the biological fluid, wherein the biosensor comprises a pair of conductors printed on the test strip to communicate with the test meter and a reagent deposited on the test strip to react with the biological fluid;
first and second contacts configured to communicate with the test meter;
first and second conductors connected to the first and second contacts, respectively;
a first plurality of diodes each having a first end connected to the first contact and a second end, wherein junction areas of the first plurality of diodes are scaled according to a binary code; and
a first plurality of resistances each having a first end connected to the second end of a respective one of the first plurality of diodes and a second end connected to the second contact,
wherein the test strip is configured to store data based on a first number of connections severed between the first plurality of resistances and the first and second conductors.

27. The test strip of claim 26, wherein values of the first plurality of resistances are scaled according to a binary code.

28. The test strip of claim 26, further comprising:
a second plurality of diodes each having a first end connected to the first contact and a second end so that the first plurality of diodes is connected to the second plurality of diodes in opposing polarity, wherein junction areas of the second plurality of diodes are scaled according to the binary code; and
a second plurality of resistances each having a first end connected to the second end of a respective one of the second plurality diodes and a second end connected to the second contact,
wherein the test strip is configured to store data based on a second number of connections severed between the first and second pluralities of resistances and the first and second conductors.

29. The test strip of claim 28, wherein values of the first plurality of resistances are scaled to be binary code, and wherein values of the second plurality of resistances are scaled according to a binary code.

30. A system comprising:
the test strip of claim 28; and
the test meter,
wherein the test meter is configured to sense the data by
supplying excitation across the first and second contacts and measuring response between the first and second contacts, and wherein the data include at least one of (i) information to calibrate the test meter and (ii) information about the test strip.

31. A system for analyzing biological fluids comprising:
a test strip comprising a biosensor to sense a biological fluid and a plurality of diodes that are connected to a plurality of contacts on the test strip and that are arranged in a network representing one of a plurality of states based on whether the diodes are short circuited, open circuited, or neither short circuited nor open circuited; and
a mobile meter configured to
supply excitation to a plurality of contacts on the test strip and measure response through the plurality of contacts,
differentiate a plurality of voltage or current levels representing the plurality of states, and
identify the one of the plurality of states represented by the network of diodes based on the measured current or voltage.

32. The system of claim 31, wherein the diodes are arranged in pairs, and wherein in each of the pairs, (i) diodes are connected in parallel, (ii) an anode of a first diode is connected to a cathode of a second diode, and (iii) a cathode of the first diode is connected to an anode of the second diode.

33. The system of claim 32, wherein in each of the pairs, a short circuit is selectively included across the first and second diodes.

34. The system of claim 31, wherein the mobile meter is configured to reverse polarity of the excitation supplied across the plurality of contacts on the test strip and measure response through the plurality of contacts.

35. The system of claim 31, wherein junction areas of the diodes are scaled to a binary code.

36. The system of claim 31, further comprising a reference diode to calibrate the system in order to supply the excitation that is compensated for temperature and diode variations.

37. The system of claim 31, further comprising a plurality of resistors to enhance differentiation of the plurality of voltage or current levels representing the plurality of states.

38. The system of claim 37, wherein the resistors are binary-weighted.

39. The system of claim 31, wherein the mobile meter is configured to communicate with the biosensor via at least one of the plurality contacts used to communicate with the diodes.

40. The system of claim 31, wherein a portion of the plurality of states stores calibration information to be used by the mobile meter.

41. A system comprising:
a test strip comprising a biosensor to sense a biological fluid and a plurality of diodes that are connected to a plurality of contacts on the test strip and that are arranged in a network representing one of a plurality of states based on whether the diodes are open circuited, wherein junction areas of the diodes are scaled to a binary code; and
a mobile meter configured to supply excitation to a plurality of contacts on the test strip and measure response through the plurality of contacts, wherein the response is distinct for each diode or a combination of diodes open circuited.

42. The system of claim 41, wherein the diodes are arranged in pairs, and wherein in each of the pairs, (i) diodes are connected in parallel, (ii) an anode of a first diode is connected to a cathode of a second diode, and (iii) a cathode of the first diode is connected to an anode of the second diode.

43. The system of claim 41, wherein the mobile meter is configured to reverse polarity of the excitation supplied across the plurality of contacts on the test strip and measure response through the plurality of contacts.

44. The system of claim 41, further comprising a reference diode to calibrate the system in order to supply the excitation that is compensated for temperature and diode variations.

45. The system of claim 41, further comprising a plurality of resistors to enhance differentiation of response for each diode or a combination of diodes open circuited.

46. The system of claim 45, wherein the resistors are binary-weighted.

47. The system of claim 45, further comprising a reference resistor to calibrate the system in order to supply the excitation that is compensated for temperature and resistor variations.

48. The system of claim 41, wherein the mobile meter is configured to communicate with the biosensor via at least one of the plurality contacts used to communicate with the diodes.

49. The system of claim 41, wherein a portion of the plurality of states stores calibration information to be used by the mobile meter.

50. A system comprising:
a test strip comprising a biosensor to sense a biological fluid and a plurality of diodes and a plurality of resistors that are connected to a plurality of contacts on the test strip and that are arranged in a network representing one of a plurality of states based on whether the diodes are short circuited, open circuited, or neither short circuited nor open circuited; and
a mobile meter configured to supply excitation to a plurality of contacts on the test strip and measure response through the plurality of contacts, wherein the response is distinct for each diode or a combination of diodes open circuited.

51. The system of claim 50, wherein the diodes are arranged in pairs, and wherein in each of the pairs, (i) diodes are connected in parallel, (ii) an anode of a first diode is connected to a cathode of a second diode, and (iii) a cathode of the first diode is connected to an anode of the second diode.

52. The system of claim 51, wherein in each of the pairs, a short circuit is selectively included across the first and second diodes, and wherein the response is distinct for each diode or a combination of diodes short circuited.

53. The system of claim 50, wherein the mobile meter is configured to reverse polarity of the excitation supplied across the plurality of contacts on the test strip and measure response through the plurality of contacts.

54. The system of claim 50, further comprising a reference resistor to calibrate the system in order to supply the excitation that is compensated for temperature and resistor variations.

55. The system of claim 50, wherein the resistors enhance differentiation of response for each diode or a combination of diodes open circuited.

56. The system of claim 50, wherein the resistors are binary-weighted.

57. The system of claim 50, further comprising a reference diode to calibrate the system in order to supply the excitation that is compensated for temperature and diode variations.

58. The system of claim 50, wherein the mobile meter is configured to communicate with the biosensor via at least one of the plurality contacts used to communicate with the diodes and resistors.

59. The system of claim 50, wherein a portion of the plurality of states stores calibration information to be used by the mobile meter.

\* \* \* \* \*